(12) United States Patent
Shemesh et al.

(10) Patent No.: US 10,545,145 B2
(45) Date of Patent: Jan. 28, 2020

(54) STOCHASTIC ARRANGEMENT OF REAGENTS IN CLUSTERS—STARC

(71) Applicant: Massachusetts Institute of Technology, Cambridge, MA (US)

(72) Inventors: Or Shemesh, Sommerville, MA (US); Asmamaw Wassie, Cambridge, MA (US); Chih-Chieh Yu, Cambridge, MA (US); Edward Boyden, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/099,248

(22) Filed: Apr. 14, 2016

(65) Prior Publication Data

US 2016/0305939 A1 Oct. 20, 2016

Related U.S. Application Data

(60) Provisional application No. 62/147,219, filed on Apr. 14, 2015.

(51) Int. Cl.
*G01N 33/566* (2006.01)
(52) U.S. Cl.
CPC ................... *G01N 33/566* (2013.01)
(58) Field of Classification Search
CPC .................................................. G01N 33/566
See application file for complete search history.

(56) References Cited

PUBLICATIONS

Podar et al. 2004; Critical role for Hck-mediated phosphorylation of Gab1 and Gab2 docking proteins in IL-6 induced proliferation and survival of MM cells. J. Bio. Chem. Manuscript M305783200, pp. 1-38.*
Sicheri et al. 1997; Crystal structure of the Src family tyrosine kinase Hck. Nature. 385: 602-609.*
Zhang et al. 2000; Phragmoplastin polymerizes into spiral coiled structures via intermolecular interaction of tow self-assembly domains. J. Bio. Chem. 275(12): 8779-8784.*
Zhang et al. 2002; Creating new fluorescent probes for cell biology. Nature Reviews. 3: 906-918.*
Lewis et al. 2011; A role for myosin VI in the localization of axonal proteins. PLoS Biology. 9(3): 1-18; a combined reference with Supplemental S2 figure describing the CD8-MVIBD sequence, optineurin sequence alignment with SEQ ID No. 3, and the DAB2 sequence.*
Lewis et al. 2009; Myosin-dependent targeting of transmembrane proteins to neuronal dendrites. Nature Neuroscience. 12(5): 568-576.*
Akerboom, J. et al., "Optimization of a GCaMP calcium indicator for neural activity imaging", J Neurosci, Oct. 3, 2012, vol. 32, pp. 13819-13840.
Arai, R. et al., "Design of the Linkers Which Effectively Separate domains of a Bifunctional Fusion Protein", Protein Engineering, 2001, vol. 14, pp. 529-532.
Broussard, G. et al., "Monitoring Activity in Neural circuits with Genetically Encoded Indicators", Frontiers in Molecular Neuroscience, Dec. 2014, vol. 7, 17 pages.
Chichili, V. et al., "Linkers in the structural biology of protein-protein interactions", Protein Science, 2013, vol. 22, pp. 153-167.
Fletcher, JM., et al., "A basis set of de novo coiled-coil peptide oligomers for rational protein design and synthetic biology", ACS Synth Biol., Jun. 15, 2012, vol. 1, pp. 240-250.
Fletcher, JM. et al., "Self-assembling cages from coiled-coil peptide modules", Science, May 3, 2013, vol. 340, pp. 595-599.
Gong, Y. et al., "High-speed recording of neural spikes in awake mice and flies with a fluorescent voltage sensor", Science, Dec. 11, 2015, vol. 350, pp. 1361-1366.
Looger, Loren and Oliver Griesbeck, "Genetically Encoded Neural Activity Indicators", Current Opinion in Neurobiology, 2012, vol. 22, pp. 18-23.
Marvin, J. et al., "An optimized fluorescent probe for visualizing glutamate neurotransmission", Nat Methods, Feb. 2013, vol. 10, pp. 162-170.
Peterka, D. et al., "Imaging voltage in neurons", Neuron, Jan. 13, 2013, vol. 69, pp. 9-21.
Reiff, D. et al., "In Vivo Performance of Genetically Encoded Indicators of Neural Activity in Flies", The Journal of Neuroscience, May 11, 2005, vol. 25, pp. 4766-4778.
Ziolkowska, NE, et al., "Organized living: formation mechanisms and functions of plasma membrane domains in yeast", Trends Cell Biol., Mar. 2012, vol. 22, pp. 151-158.

\* cited by examiner

*Primary Examiner* — Karen Cochrane Carlson
(74) *Attorney, Agent, or Firm* — Pierce Atwood LLP

(57) ABSTRACT

The invention, in some aspects relates to compositions and methods for imaging biological systems and physiological activity and conditions in cells.

19 Claims, 10 Drawing Sheets

Specification includes a Sequence Listing.

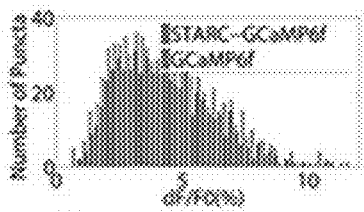
Fig. 4E                    Fig. 4F                    Fig. 4G
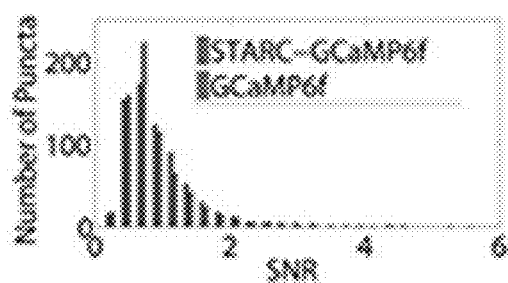
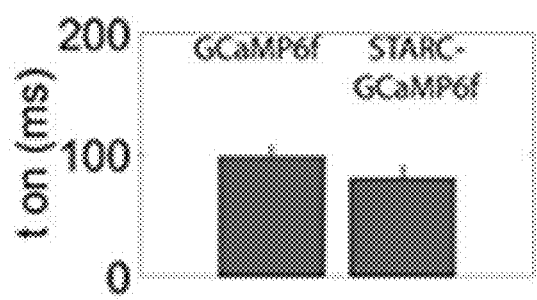
Fig. 4H                    Fig. 4I
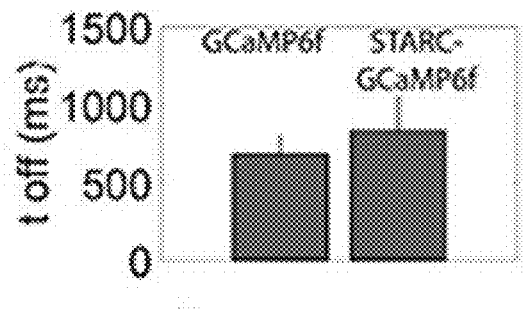
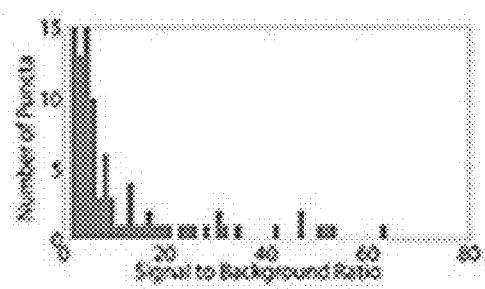
Fig. 4J                    Fig. 4K

SEQUENCE LISTING

<160> NUMBER OF SEQ ID NOS: 3

<210> SEQ ID NO 1
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 1

Arg Asp Gln Pro Leu Asn Ser Lys Lys Lys Arg Leu Leu Ser Phe
1               5                   10                  15

Arg Asp Val Asp Phe Glu Glu Asp Ser Asp
            20                  25

<210> SEQ ID NO 2
<211> LENGTH: 178
<212> TYPE: PRT
<213> ORGANISM: Artificial Sequence
<220> FEATURE:
<223> OTHER INFORMATION: Synthetic polypeptide

<400> SEQUENCE: 2

Lys Val Asp Lys Met Leu Leu Gln Glu Leu Ser Glu Lys Leu Glu Leu
1               5                   10                  15

Ala Glu Gln Ala Leu Ala Ser Lys Gln Leu Gln Met Asp Glu Met Lys
                20                  25                  30

Gln Thr Leu Ala Lys Gln Glu Glu Asp Leu Glu Thr Met Ala Val Leu
            35                  40                  45

Arg Ala Gln Met Glu Val Tyr Cys Ser Asp Phe His Ala Glu Arg Ala
    50                  55                  60

Ala Arg Glu Lys Ile His Glu Glu Lys Glu Gln Leu Ala Leu Gln Leu
65                  70                  75                  80

Ala Ile Leu Leu Lys Glu Asn Asn Asp Ile Glu Glu Gly Gly Ser Arg
                85                  90                  95

Gln Ser Leu Met Glu Met Gln Cys Arg His Gly Val Lys Glu Met Phe
            100                 105                 110

Lys Asp Phe Gln Leu Arg Gln Pro Pro Leu Val Pro Ser Arg Lys Gly
        115                 120                 125

Glu Thr Pro Pro Ser Gly Thr Ser Ser Ala Phe Ser Ser Tyr Phe Asn
    130                 135                 140

Asn Lys Val Gly Ile Pro Gln Glu His Val Asp His Asp Asp Phe Asp
145                 150                 155                 160

Ala Asn Gln Leu Leu Asn Lys Ile Asn Glu Pro Pro Lys Pro Ala Pro
                165                 170                 175

Arg Gln

<210> SEQ ID NO 3
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 3

Gly Gly Ser Gly Gly Thr Gly Gly Ser Gly Gly Thr
1               5                   10

STOCHASTIC ARRANGEMENT OF REAGENTS IN CLUSTERS—STARC

RELATED APPLICATIONS

This application claims benefit under 35 U.S.C. § 119(e) of U.S. Provisional application Ser. No. 62/147,219 filed Apr. 14, 2015, the disclosure of which is incorporated by reference herein in its entirety.

GOVERNMENT INTEREST

This invention was made with government support under the NIH 1R01NS087950, NIH 1U01MH106011-01, and NIH 1DP1NS087724 grants awarded by the National Institutes of Health. The Government has certain rights in the invention.

FIELD OF THE INVENTION

The invention, in some aspects, relates to compositions and methods for clustering and distributing genetically encoded activity reporters in cells, tissues, and subjects.

BACKGROUND OF THE INVENTION

Imaging within cells and biological systems is used to examine cell activity but it has not been possible to image cells and biological systems with high speed and nanoscale precision.

SUMMARY OF THE INVENTION

The invention, in part, relates imaging methods that permit imaging of physiology of multiple cell types with subcellular, nanoscale precision. The invention, in part, includes methods and compounds (for example, polypeptides and polynucleotides) that can be prepared and utilized to enable extremely sensitive imaging within cells. The invention, in part, includes expressing in one or more cells a fluorescent indicator molecule comprising a polypeptide that causes clustering of the expressed fluorescent indicator molecule, wherein the distance between the fluorescent indicator molecule clusters is greater than the resolving distance of the microscope used to image the one or more cells, which permits cells that pass within this resolving distance to be imaged separately. The separate imaging is possible because the clusters "sample" the different cells and allow their physiology to be determined at points greater than the diffraction limit, even though they pass within a diffraction limit of each other. Embodiments of imaging methods of the invention comprise clustering of and stochastically distributing genetically encoded activity reporters inside neurons. The clusters fall more than a diffraction limit apart than one another and when neural processes that fall within a diffraction limit are active, their activity is detectable and discernible by an optical microscope. In certain embodiments of the invention, neurons expressing the stochastic arrangement of reagents in clusters of GCaMP6f (STARC-GCaMP6f) also express immunoepitopes in a mosaic pattern, meaning different neurons express different immunoepitopes. Following live imaging experiments, the neurons can be fixed and imaged using ExM and each cluster can be attributed to a certain cell. Thus, using methods of the invention, it is known exactly which neural processes were active within a sub-diffraction space: clusters that are far apart from each other, but that are located within very thin processes that touch, will allow sampling of these nanoscale domains with conventional microscopy.

According to an aspect of the invention, compositions are provided. The compositions include a genetically encoded activity reporter, wherein the genetically encoded activity reporter comprises two or more binding repeat polypeptides that self-polymerize when expressed, an indicator polypeptide, and a linker polypeptide. In some embodiments, the indicator polypeptide is a voltage indicator polypeptide, a calcium indicator polypeptide, a potassium indicator polypeptide, a pH indicator polypeptide, or a magnesium indicator polypeptide. In certain embodiments, the indicator polypeptide is an opsin or a GCaMP6f polypeptide or a functional variant thereof. In some embodiments, the binding repeat polypeptides comprise one or more polypeptides that bind with each other when expressed in a cell. In some embodiments, the binding repeat polypeptide is a myosin peptide. In certain embodiments, the two or more binding repeats comprise at least one of myosin 5a polypeptide and one of a myosin 6 polypeptide. In some embodiments, the binding repeat polypeptide comprises a coiled coil polypeptide. In some embodiments, the linking polypeptide is positioned between the indicator polypeptide and a binding repeat polypeptide. In some embodiments, when expressed in a cell, the indicator polypeptide is soluble in the cell. In certain embodiments, when expressed in a cell, the indicator polypeptide is a membranal polypeptide. In some embodiments, when the genetically encoded activity reporter is expressed in a cell, imaging the genetically encoded activity reporter determines one or more aspects of the cell's physiology. In certain embodiments, the indicator polypeptide comprises a fluorescent polypeptide. In some embodiments, the binding of the binding polypeptides with each other results in a cluster of the binding polypeptides and the cluster determines a distance between the indicator polypeptide of the expressed genetically encoded activity reporter and an indicator polypeptide of a second expressed genetically encoded activity reporter. In some embodiments, the distance is greater than a diffraction limit of a microscope. In some embodiments, the expressed genetically encoded activity reporter is visualized with the microscope. In certain embodiments, when the genetically encoded activity reporter is expressed in a cell, imaging the genetically encoded activity reporter allows a process or condition of the cell's physiology to be determined, wherein the process or condition determined is a process or condition indicated by the indicator polypeptide. In some embodiments, imaging the genetically encoded activity reporter allows a change in the process or condition to be determined. In some embodiments, the process or condition in the cell's physiology is one or more of: the: pH, the voltage, and the presence of calcium, magnesium, chloride, or potassium in the cell.

In another aspect of the invention, fusion proteins are provided that include the expressed genetically encoded activity reporter polypeptide in any embodiment of the aforementioned aspect of the invention.

In yet another aspect of the invention, polynucleotides are provided that encode the composition of any embodiment of any aforementioned aspect of the invention.

In another aspect of the invention, expression vectors are provided that include a polynucleotide of an embodiment of any of the aforementioned aspects of the invention.

According to another aspect of the invention, methods of imaging in a cell are provided, the methods including: expressing in a first cell, one or more genetically encoded activity reporter genetically encoded activity reporter, wherein the genetically encoded activity reporter comprises two or more binding repeat polypeptides that self-polymerize when expressed, an indicator polypeptide, and a linker polypeptide, and imaging the first cell with a microscope. In some embodiments, the method also includes expressing in one or a plurality of additional cells one or more of a genetically encoded activity reporter, wherein the genetically encoded activity reporter comprises two or more binding repeat polypeptides that self-polymerize when expressed, an indicator polypeptide, and a linker polypeptide; and imaging the first cell and one or more of the additional cells with a microscope. In certain embodiments, the one or more cell of the first cell, the one additional cell, and the plurality additional cells are in or have been obtained from: cell culture, tissue culture, or a subject. In some embodiments, a distance between each of two or more of the indicator polypeptides expressed in the first cell is greater than a diffraction limit of the microscope. In certain embodiments, a distance between the one or more indicator polypeptides expressed in the first cell, the one additional cell, and the plurality of additional cells is greater than a diffraction limit of the microscope. In some embodiments, the one or more genetically encoded activity reporters that pass within the microscope's resolving distance are imaged separately from each other. In some embodiments, the genetically encoded activity reporter expressed in at least one cell comprises a polypeptide set forth herein as STARC-GCaMP6f. In certain embodiments, the genetically encoded activity reporter expressed in the first cell comprises a different amino acid sequence than the amino acid sequence of the genetically encoded activity reporter expressed in the second cell. In some embodiments, the method also includes detecting one or more immunoepitopes in one or more cells in which a genetically encoded activity reporter is expressed. In some embodiments, the method also includes determining a pattern of expression of one or more of the immunoepitopes in one or more cells in which a genetically encoded activity reporter is expressed. In some embodiments, the indicator polypeptide is a voltage indicator polypeptide, a calcium indicator polypeptide, a potassium indicator polypeptide, a pH indicator polypeptide, or a magnesium indicator polypeptide. In certain embodiments, the indicator polypeptide is an opsin or a GCaMP6f polypeptide or a functional variant thereof. In some embodiments, the binding repeat polypeptides comprise two or more polypeptides that bind with each other when expressed in a cell. In some embodiments, at least one of the binding repeat polypeptide is a myosin peptide. In some embodiments, the two or more binding repeats comprise at least one of myosin 5a polypeptide and one of a myosin 6 polypeptide. In certain embodiments, the binding repeat polypeptide comprises a coiled coil polypeptide. In some embodiments, the linking polypeptide is positioned between the indicator polypeptide and a binding repeat polypeptide. In some embodiments, the indicator polypeptide is soluble in the cell. In some embodiments, the indicator polypeptide is a membranal polypeptide. In certain embodiments, the genetically encoded activity reporter determines one or more aspects, activities, and alterations of the cell's physiology. In some embodiments, the indicator polypeptide comprises a fluorescent polypeptide. In some embodiments, the binding of the binding polypeptides with each other results in a cluster of the binding polypeptides, and the cluster determines a distance between the indicator polypeptide of the expressed genetically encoded activity reporter and an indicator polypeptide of a second expressed genetically encoded activity reporter. In some embodiments, the distance is greater than a diffraction limit of a microscope. In certain embodiments, the expressed genetically encoded activity reporter is visualized with the microscope. In some embodiments, when the genetically encoded activity reporter is expressed in a cell, imaging the genetically encoded activity reporter allows a process or condition of the cell's physiology to be determined, wherein the process or condition determined is a process or condition indicated by the indicator polypeptide. In some embodiments, imaging the genetically encoded activity reporter allows a change in the process or condition to be determined. In some embodiments, the process or condition in the cell's physiology is one or more of: the: pH, the voltage, and the presence of calcium, magnesium, chloride, or potassium in the cell. In certain embodiments, the genetically encoded activity reporter that is expressed in the cell is a fusion protein. In some embodiments, the genetically encoded activity reporter is expressed in the cell from a vector comprising a polynucleotide sequence that encodes the genetically encoded activity reporter.

According to yet another aspect of the invention, methods assessing a process or condition in a cell are provided. The methods including: (a) expressing in a cell, a genetically encoded activity reporter, wherein the genetically encoded activity reporter comprises two or more binding repeat polypeptides that self-polymerize when expressed, an indicator polypeptide, and a linker polypeptide; (b) imaging the genetically encoded activity reporter in the cell; and (c) assessing a process or condition in the cell, based at least in part on the imaging of the indicator polypeptide of the genetically encoded activity reporter in the cell. In some embodiments, the imaging the genetically encoded activity reporter allows a change in the process or condition to be determined. In certain embodiments, the indicator polypeptide is a voltage indicator polypeptide, a calcium indicator polypeptide, a potassium indicator polypeptide, a pH indicator polypeptide, or a magnesium indicator polypeptide. In some embodiments, the indicator polypeptide is an opsin or a GCaMP6f polypeptide or a functional variant thereof. In some embodiments, the process or condition in the cell is one or more of: the: pH, the voltage, and the presence of calcium, magnesium, chloride, or potassium in the cell. In some embodiments, the genetically encoded activity reporter that is expressed in the cell is a fusion protein. In certain embodiments, the genetically encoded activity reporter is expressed in the cell from a vector comprising a polynucleotide sequence that encodes the genetically encoded activity reporter. In some embodiments, the binding repeat polypeptides comprise two or more polypeptides that bind with each other when expressed in a cell. In some embodiments, the binding repeat polypeptide is a myosin peptide. In certain embodiments, the two or more binding repeats comprise at least one of myosin 5a polypeptide and one of a myosin 6 polypeptide. In some embodiments, the binding repeat polypeptide comprises a coiled coil polypeptide. In some embodiments, the indicator polypeptide is soluble in the cell or is a membranal polypeptide.

According to another aspect of the invention, methods of determining an effect of a candidate agent on a process or condition in a cell are provided. The methods including: (a) expressing in a cell, a genetically encoded activity reporter, wherein the genetically encoded activity reporter comprises two or more binding repeat polypeptides that self-polymerize when expressed, an indicator polypeptide, and a linker polypeptide; (b) contacting the expressed genetically encoded activity reporter with a candidate agent; (c) imaging the genetically encoded activity reporter in the cell; (d)

assessing a process or condition in the cell, based at least in part on the imaging of (c); (e) comparing the assessment of (d) with a control assessment of the process or condition; wherein a difference between the process or condition in the cell as assessed in (d) and the control assessment of the process or condition determines an effect of the candidate agent on the process or condition in the cell. In certain embodiments, the genetically encoded activity reporter expressed in at least one cell comprises a polypeptide set forth herein as STARC-GCaMP6f. In some embodiments, the method also includes detecting one or more immunoepitopes in one or more cells in which the genetically encoded activity reporter is expressed. In certain embodiments, the method also includes determining a pattern of expression of one or more of the immunoepitopes in one or more cells in which a genetically encoded activity reporter is expressed. In some embodiments, the indicator polypeptide is a voltage indicator polypeptide, a calcium indicator polypeptide, a potassium indicator polypeptide, a pH indicator polypeptide, or a magnesium indicator polypeptide. In certain embodiments, the indicator polypeptide is an opsin or a GCaMP6f polypeptide or a functional variant thereof. In some embodiments, the binding repeat polypeptides comprise two or more polypeptides that bind with each other when expressed in a cell. In some embodiments, the binding repeat polypeptide is a myosin peptide. In certain embodiments, the two or more binding repeats comprise at least one of myosin 5a polypeptide and one of a myosin 6 polypeptide. In some embodiments, the binding repeat polypeptide comprises a coiled coil polypeptide. In some embodiments, the indicator polypeptide is soluble in the cell. In certain embodiments, the indicator polypeptide is a membranal polypeptide. In some embodiments, the genetically encoded activity reporter determines one or more aspects, activities, and alterations of the cell's physiology. In some embodiments, the indicator polypeptide comprises a fluorescent polypeptide. In certain embodiments, the binding of the binding polypeptides with each other results in a cluster of the binding polypeptides, and the cluster determines a distance between the indicator polypeptide of the expressed genetically encoded activity reporter and an indicator polypeptide of a second expressed genetically encoded activity reporter. In some embodiments, the distance is greater than a diffraction limit of a microscope. In certain embodiments, the expressed genetically encoded activity reporter is visualized with a microscope.

BRIEF DESCRIPTION OF THE DRAWINGS

FIG. 1B shows molecular strategies for achieving STARC. FIG. 1B, left panel shows fusing optogenetic tools with myosin 6 and 5 tandem repeats. The myosin repeats lead to clustering of their cargos across neurites in the cell. Right: Coiled-Coil Induced Clustering of genetically encoded sensors. The homo-oligomerizing coiled-coils are fused to the N and C termini of sensors inducing the clustering of the sensors. While the clustering of cytosolic sensors is induced in the cytoplasm, genetically encoded voltage sensors form clusters in the membrane. Such a sensor polypeptide is referred to herein as a "membranal polypeptide".

FIG. 2A is a photomicrograph of a wide-field image of cultured hippocampal neurons expressing STARC-GCaMP6f. The analyzed area denoted by the rectangle shown within the image. FIG. 2B is a photomicrograph of a binary image with somatic clusters removed. FIG. 2C is a photomicrograph of a df/f map showing field of view with color-coded response of each cluster. The hue denotes the maximum response ($\Delta F_{max}/F$) recorded from a cluster during the 100 s time increment. FIG. 2D top graph shows the size of each cluster. FIG. 2D bottom graph shows the size distribution of clusters in field of view. FIG. 2E is a brightness histogram of clusters (brightness is given in arbitrary units). FIG. 2F is a maximum response ($\Delta F_{max}/F$) cluster histogram. FIG. 2G is an image shows a single-trial time-response of clusters. Each row shows the-time response of a cluster with the color hue denoting percent fluorescence change ($\Delta F/F$). FIG. 2H is a graph showing signal-to-noise ratio distribution among clusters. The signal-to-noise ratio was calculated as amplitude/1× standard deviation of signal. FIG. 2I is a graph showing the Matrix of Correlation values between clusters. Color denotes the degree of correlation (Pearson's R) between any two clusters. Scaling is indicated on the right. Scale bar=10 μm for A-C.

FIG. 3A-D show results obtained when primary hippocampal neurons were cultured and transfected with mCherry (FIG. 3A) and STARC-GCaMP6f (FIG. 3B). Merge image is given in FIG. 3C. FIG. 3D is a zoomed-in image based on the inset in FIG. 3C. FIG. 3E-I shows results obtained when primary hippocampal neurons were cultured and transfected with STARC-GCaMP6f. FIGS. 3E, 3F, 3G, 3H, and 3I show immunostaining visualization of the endoplasmic reticulum, Golgi apparatus, early endosomes, mitochondria, and lysosomes, respectively.

FIG. 4A is a wide-field Image of a cultured hippocampal neuron expressing STARC-GCamp6f. FIG. 4C, middle panel shows the time-response of all clusters. FIG. 4C, bottom panel shows the average time response of all clusters in the cell. FIG. 4E shows the distribution of nearest neighbor distances of clusters. FIG. 4F shows brightness histograms in STARC-GCaMP6 cells and control cells. FIG. 4G shows the maximum response to one action potential ($\Delta F_{max}/F$) histogram for STARC-GCaMP6f clusters and GCaMP6f. FIG. 4H shows a Signal-to-Noise ratio (SNR) distribution among STARC-GCaMP6f clusters and GCaMP6f clusters. FIG. 4I shows fluorescence rise time (Ton) of STARC-GCaMP6f and GCaMP6f. FIG. 4J shows fluorescence decay time (Toff) of STARC-GCaMP6f and GCaMP6f. FIG. 4K shows signal to background distribution for 100 clusters, from 4 different cells for 1 action potential. FIG. 4N shows the time-response of all clusters. Each row shows the time response of a cluster with the color hue denoting percent fluorescence change (ΔF/F0).

FIG. 5A shows results obtained from in vitro culture of mice hippocampal neurons co-expressing STARC-GCaMP6f (green) and mCherry (red). FIG. 5B is an expanded view of a representative region from FIG. 5A (inset). Three STARC-GCaMP6f puncta of interest are denoted by white arrowheads (P1, P2, P3). The cells were imaged for 50 s and activity was recorded. FIG. 5C-D demonstrates that expansion microscopy enhances resolution of closely located neural processes, enabling unambiguous attribution of STARC-GCaMP6f puncta. FIG. 5C shows post-expanded area of interest that corresponds to FIG. 5A. FIG. 5D shows post-expanded area of interest that corresponds to FIG. 5B. FIG. 5E shows activity plots of the STARC-GCaMP6f puncta of interest after attribution to cell 1 and cell 2. Scale bars: 10 μm in FIGS. 5A and B, pre-expanded, 10 μm in FIGS. 5C and D, post-expanded (physical size post expansion is 45 μm).

FIG. 6A shows the field of view at 10 seconds. FIG. 6B shows the field of view after 35 seconds. FIG. 6C shows an overlay of FIG. 6A and FIG. 6B. FIG. 6D shows an expanded view of the insert in FIG. 6C and shows the response of single puncta during the experiment. The localization of puncta 1-4 is denoted in numbers in FIG. 6E. FIG. 6F provides an overlay of the responses of puncta 1-4 over time. The grating stimuli are given on the x axis. FIG. 6G provides a df/f0 analysis of the responses of all puncta in the field of view during the experiment.

FIG. 7A shows imaged neuron expressing STARC-GCaMP6. FIG. 7B shows the same neuron, imaged again 50 minutes after the image of FIG. 7A. FIG. 7C is an overlay of the FIGS. 7A and 7B images (T=0, 50 min in green and red respectively) showing that the movement of STARC-GCaMP6 puncta is negligible.

BRIEF DESCRIPTION OF THE SEQUENCES

Figure 1A:
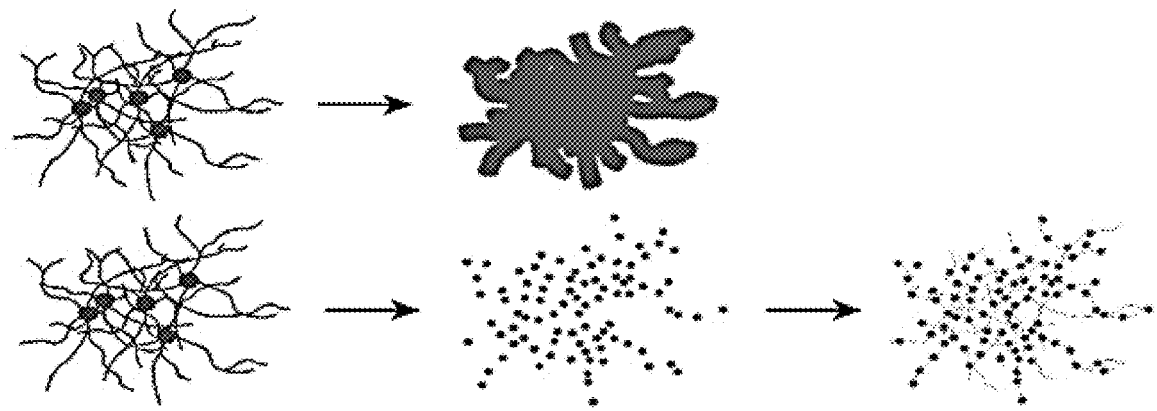
FIG. 1A-B shows schematic diagrams illustrating stochastic arrangement of reagents in clusters-STARC methods. The FIG. 1A top row illustrates that imaging optical sensors expressed in the in vivo brain (left) result in an image where parts of different cells cannot be resolved because they make contacts within a diffraction limited space owing to the compact architecture of the brain (right). The FIG. 1A bottom row illustrates that to enable imaging of multiple neurons (left panel) with subcellular resolution, optical reagents are arranged into clusters which are spaced at least a diffraction limited distance apart (middle panel). Subsequently, these clusters can be associated with cells via super-resolution imaging (right panel).

SEQ ID NO: 1 is MBD amino acid sequence:
RDQPLNSKKKKRLLSFRDVDFEEDSD.

SEQ ID NO: 2 is MVIBD amino sequence:
KVDKMLLQELSEKLELAEQALASKQLQMDEMKQTLAKQEEDLETMAVLRA

QMEVYCSDFHAERAAREKIHEEKEQLALQLAILLKENNDIEEGGSRQSLM

EMQCRHGVKEMEKDFQLRQPPLVPSRKGETPPSGTSSAFSSYFNNKVGIP

QEHVDHDDFDANQLLNKINEPPKPAPRQ.

SEQ ID NO: 3 a linker amino acid sequence
GGSGGTGGSGGT.

DETAILED DESCRIPTION

Methods and compounds have now been developed for spatially discretizing neural activity reporters in a cell, by stochastically arranging activity reporters in clusters (STARC) and distributing them throughout the neuron's processes. Analysis of STARC-GCaMP6f compounds in embodiments of imaging methods of the invention, have demonstrated that its brightness, sensitivity and kinetics are minimally different from that of unmodified GCaMP6f. STARC imaging compounds have been used to record neural activity in dense neuronal networks, and expansion microscopy has also been applied to unambiguously attribute clusters and their associated activity to individual neurons in the network. It has now been shown that STARC-GCaMP6f puncta expressed in mouse primary visual cortex can report neural activity in vivo in response to visual stimuli. By discretizing activity reporters in a cell, STARC methods provide a widely applicable strategy for mapping neural dynamics both at sub-cellular resolution over an entire cell, and at sub-diffraction limit resolution over dense neuronal circuits such as the mammalian brain.

The invention in some aspects relates to novel methods of imaging that permit imaging of the physiology and activity within different cell types with subcellular, nanoscale precision. The methods, in some aspects include clustering and stochastically distributing genetically encoded activity reporters inside cells to be imaged. In certain embodiments, the genetically encoded activity reporter includes, but is not limited to, a genetically encoded calcium indicator (GECI), a non-limiting example of which is GCaMP6f. In certain embodiments of the invention, the cells to be imaged include but are not limited to neurons, muscle cells, epithelial cells, or other suitable cells. In certain aspects of the invention, the cell is an excitable cell.

When expressed in a cell, STARC polypeptide molecules form clusters that are located more than a diffraction limit apart than one another. This way, when neural processes that fall within a diffraction limit are active, their activity is detectable and discernible by an optical microscope. As used herein the term "diffraction limit" used in reference to a imaging means the resolving distance of a microscope. Neurons that express a stochastic arrangement of reagents in clusters of the invention, also may express immunoepitopes in a mosaic pattern, meaning different neurons express different immunoepitopes. The localization of the different immunoepitopes can be detected using immunodetection methods thus permitting identification and localization of different cells and processes. As a non-limiting example, GCaMP6f (STARC-GCaMP6f) and another STARC compound that has different immunoepitopes that STARC-GCaMP6f can be expressed in a brain and immunodetection methods using antibodies raised against different immunoepitopes of the two STARC compositions can be used to identify and compare their locations. Following live imaging experiment, neurons may be fixed and imaged using expansion microscopy (ExM) and each cluster is attributed to a certain cell. Methods and compounds of the invention permit determination of exactly which neural processes are active within a sub-diffraction space: clusters that are far apart from each other, but that are located within very thin processes that touch, allow sampling of these nanoscale domains with conventional microscopy.

STARC Molecules, Compounds, and Variants

A genetically encoded activity reporter of the invention, which is also referred to herein as a "STARC imaging compound" of the invention, comprises a genetically encoded indicator molecule, a linker molecule, and a binding repeat molecule. Binding repeat molecules of an expressed STARC polypeptide bind to each other, (also referred to herein as "self-polymerize") forming a cluster of the binding polypeptides that is attached to the indicator polypeptide via the linker polypeptide of the STARC polypeptide. Physical features of a cluster, such as its volume, diameter, inter polypeptide distance, etc., result in a sufficient distance between the clusters of any two expressed STARC imaging compounds of the invention to permit resolution and distinct imaging of each indicator polypeptide. Expressed STARC imaging compounds of the invention thus appear as puncta when visualized using methods of the invention. In certain aspects of the invention, an indicating polypeptide in a STARC polypeptide compound expressed in a cell, tissue or subject is positioned more than a diffraction limit apart from an indicating polypeptide of another expressed STARC imaging polypeptide. As used herein, the term "puncta" used in reference to STARC imaging methods of the invention means a discrete, clearly delineated point wherein the indicator of the STARC imaging polypeptide is visible. Thus, in a cell or tissue in which one or more STARC imaging compounds of the invention are expressed, the indicator polypeptide of each expressed STARC imaging polypeptide can be separately resolved from other expressed STARC imaging polypeptides, at least in part, because the size of the STARC clusters result in a distance of at least a diffraction limit between any two expressed STARC indicator polypeptides.

STARC imaging compounds of the invention may include a genetically encoded indicator; 1, 2, 3, 4, 5, 6, 7, 8, 9, 10, or more binding repeats; and one or more linker sequences. As used herein, the term "STARC molecule" means a STARC imaging polypeptide or its encoding polynucleotide. The term STARC molecule may refer to a STARC molecule that includes a genetically encoded indicator, one or more linker sequences, and binding repeat sequences, and may refer to the full STARC molecule, or to a portion of the full STARC molecule. For example, genetically encoded indicator molecules, linker molecules, and binding molecules that are included in STARC imaging molecules of the invention may each be referred to individually herein as STARC indicator molecules, STARC linker molecules, and STARC binding molecules, respectively. A STARC imaging compound of the invention may in some embodiments, comprises a STARC molecule and one or more additional polynucleotide sequences, polypeptide sequences, detectable labels, trafficking sequences, etc. STARC-GCaMP6f is a non-limiting example of a STARC imaging molecule of the invention that may be included in compositions of the invention and used in embodiments of imaging methods of the invention.

A STARC polypeptide of the invention that is expressed in a cell may be soluble or may be positioned in a membrane of the cell. As used herein a polypeptide that is positioned in a membrane of a cell is also referred to as a "membranal polypeptide" or a "membrane polypeptide". In certain aspects of the invention, the location of a STARC imaging compound expressed in a cell may result from the cellular localization of the expressed indicator polypeptide in the STARC imaging compound. For example, a genetically encoded voltage sensor or opsin molecule may be positioned in a membrane of the cell in which it is expressed thereby resulting in the position of the STARC imaging compound in the cell. Similarly, a STARC imaging compound comprising a soluble calcium sensor molecule may be positioned in the cytoplasm of the cell in which it is expressed. The term "indicator" used herein in reference to molecules, compounds, polypeptides and encoding polynucleotides, is used interchangeably with the term "sensor". In certain aspects of the invention, an indicator polypeptide comprises a detectable label that can be visualized, for example using microscopy. It will be understood that in certain aspects of the invention, visualization of an indicator polypeptide expressed in a cell, corresponds to a physiological aspect of, alteration in, change of process in, and/or activity in the cell for which the indicator polypeptide is selected. For example, to detect in a cell aspects, alternations, or activities such as: ion flux, pH change, voltage change, presence or change in calcium, magnesium, potassium, chloride, etc. an indicator polypeptide that functions to detect one or more of such aspects, alternations, and activities would be included in a STARC imaging compound expressed in the cell.

STARC Imaging Compound Components—Indicator, Binding, and Linker Molecules

A STARC imaging compound of the invention may comprise an indicator molecule, such as a genetically encoded indicator molecule, its encoding polynucleotide, or variants thereof. Non-limiting examples of genetically encoded indicator molecules that may be included in embodiments of STARC imaging molecules of the invention are: calcium indicators, voltage indicators, magnesium indicators, chloride indicators, opsins, and pH indicators. Non-limiting examples of genetically encoded calcium indicators include: GCaMP6f, GCaMP6, GCaMP5G, GCaMP6G, GCaMP3G, jRCaMP1, and jRGECO1 molecules, and functional variants thereof. A non-limiting example of a STARC compound of the invention is a STARC-GCaMP6 polypeptide having a sequence as follows: GCaMP6f (amino acid sequence)-GGSGGTGGSGGT (SEQ ID NO:3)-MVIBD (SEQ ID NO:2)-MBD (SEQ ID NO:1)-MVIBD (SEQ ID NO:2)-MBD (SEQ ID NO:1)-MVIBD (SEQ ID NO:2)-MBD (SEQ ID NO:1). In certain aspects of the invention a genetically encoded indicator molecule may refer to an indicator polypeptide, its encoding polynucleotide, or functional variants thereof. These and other genetically encoded indicators are known and routinely used in the art and may be included in compositions and methods of the invention. (See for example: Looger, L. L. & O. Griesbeck, 2012 Current Opinion in Neurobiology, Volume 22, Issue 1, Pages 18-23; Reiff, D. F. J Neurosci. 2005 May 11; 25(19): 4766-4778; Broussard, G. et al. 2015 Frontiers in Mol. Neurosci. December 5: Vol. 7, Article 91; Peterka, D. S. et al. 2011 Neuron 69(1):9-21; and Marvin J. S. et al. 2013 Nature Methods. 10(2):162-170, each of which is incorporated herein by reference.)

A STARC imaging molecule of the invention may comprise 1, 2, 3, 4, 5, 6, 7, 8, 9, 10, or more binding repeat molecules (also referred to herein as "binding molecules"). A non-limiting example of a binding repeat that may be included in an imaging compound of the invention is a myosin binding repeat. In certain aspects of the invention the term "binding molecule" used in reference to a binding repeat molecule may be a binding polypeptide, its encoding polynucleotide, or functional variants thereof. A binding repeat may include 2, 3, 4, 5, 6, 7, 8, 9, 10, or more binding molecules that bind to each other (also referred to herein as "to self-bind" and "to oligomerize with each other") when expressed in a cell as part of a STARC imaging polypeptide of the invention. Self-bound, oligomerized binding polypeptides of a STARC imaging compound of the invention form a binding polypeptide cluster in the cell in which the STARC imaging compound is expressed. Coiled coil polypeptides may also be used as binding molecules in embodiments of compounds and methods of the invention. Additional binding polypeptides and their encoding polynucleotides are known in the art and may be included in compositions and methods of the invention. Non-limiting examples of binding molecules that may be used in aspects of the invention are: myosin binding repeats including but not limited to: binding repeats of myosin 5a (MBD) set forth herein as SEQ ID NO 1, and functional variants thereof and binding repeats of myosin 6 (MVIBD) set forth herein as SEQ ID NO: 2, and functional variants thereof. Additional art-known binding molecules may be used in aspects for the invention, including but not limited to coiled coils binding molecules, and eisosomes. See for example: Fletcher J. M. et al ACS Synth Biol. 2012 Jun. 15; 1(6):240-50; Fletcher J. M et al Science. 2013 May 3; 340(6132):595-9; and Ziolkowska, N. E. Trends Cell Biol. 2012 March; 22(3):151-8, the contents of each is incorporated herein by reference.

A STARC imaging molecule of the invention comprises one or more linker molecules that may be positioned between a genetically encoded indicator molecule and binding molecule repeats of the STARC imaging molecule. When a STARC imaging compound of the invention is expressed in a cell, a linker polypeptide attaches the binding polypeptide cluster to the indicator polypeptide. In some aspects of the invention a linker polypeptide attached a soluble indicator polypeptide and a cluster of binding polypeptides in an expressed STARC imaging compound. In certain embodiments of the invention, a linker molecule connects a membrane-positioned indicator polypeptide and a cluster of binding polypeptides in an expressed STARC imaging compound.

Non-limiting examples of linker molecules that may be included in STARC imaging compounds and methods of the invention are SEQ ID NO: 3 and variants thereof, and their encoding polynucleotide sequences. In certain aspects of the invention the term "linker molecule" may refer to a linker polypeptide, its encoding polynucleotide, or functional variants thereof. A linker polypeptide of the invention may be a flexible linker or a rigid linker and may include at least 2, 3, 4, 5, 6, 7, 8, 9, 10, 11, 12, 13, 14, 15, 16, 17, 18, 19, 20, 25, 30, 25, or 40 amino acids. Non-limiting examples of polypeptide linker sequences that may be used in STARC imaging compounds and methods of the invention are polypeptide set forth as SEQ ID NO: 3 GGSGGTGGSGGT and functional variants thereof. Additional linker polypeptides and their encoding polynucleotides are known and routinely used in the protein arts and may be included in some embodiments of compositions and methods of the invention. (See for example: Chichili, V. P. R, et al., Protein Science 2013 Vol 22:153-167; Chen, X. et al., Adv Drug Deliv Rev. 2013 Oct. 15; 65(10): 1357-1369; and Arai et al. Protein Eng. 2001 August; 14(8):529-32, each of which is incorporated herein by reference.)

A non-limiting example of a STARC imaging molecule of the invention is the STARC-GCaMP polypeptide. The STARC-GCaMP molecule includes a GCaMP6f polypeptide—a 12 amino acid linker [GGSGGTGGSGGT (SEQ ID NO:3)]—and binding repeats: MVIBD-MBD-MBD-MBD, wherein MBD is a myosin 5a polypeptide set forth herein as SEQ ID NO 1 and MVIBD is a myosin 6 polypeptide set forth herein as SEQ ID NO: 2. STARC-GCaMP6f molecules and functional variants thereof are non-limiting examples of embodiments of STARC imaging molecules that can be prepared and included in compounds and compositions of the invention and can be used in imaging methods of the invention. Additional STARC imaging molecules and compounds may be prepared and used in methods of the invention.

Cells and Subjects

Some aspects of the invention include STARC imaging methods and compounds and components used in one or more cells to image biological systems, activity, alterations, etc. within the one or more cells. Compounds and methods of the invention may be used in prokaryotic and eukaryotic cells. Compounds and methods of the invention can also be used in artificial cells. In certain embodiments of the invention, a cell that can be imaged using compounds and methods of the invention is a mammalian cell; including but not limited to cells of humans, non-human primates, dogs, cats, horses, rodents, etc. In some embodiments of the invention, method of the invention may be used in non-mammalian cells; including but not limited to insect cells, avian cells, fish cells, invertebrate cells, single-cell organisms, plant cells, etc. Imaging compounds and method of the invention may be used in non-excitable cells and in excitable cells, the latter of which includes cells able to produce and respond to electrical signals. Examples of excitable cell types include but are not limited, to neurons, muscle cells, cardiac cells, and secretory cells (such as pancreatic cells, adrenal medulla cells, pituitary cells, etc.). As used herein the term "plurality" when used in context of cells, means two or more cells.

Non-limiting examples of cells that may be used in methods of the invention include: neuronal cells, nervous system cells, cardiac cells, circulatory system cells, connective tissue cells, visual system cells, auditory system cells, secretory cells, endocrine cells, and muscle cells. In some embodiments, a cell used in conjunction with an imaging method of the invention may be a healthy normal cell, which is not known to have a disease, disorder, or abnormal condition. In some embodiments, a cell used in conjunction with a method of the invention may be an abnormal cell, for example, a cell that is believed to have, or has been has been diagnosed as having, a disorder, disease, or condition, including, but not limited to a degenerative cell, a neurological disease-bearing cell, a cell model of a disease or condition, an injured cell, etc. In some embodiments of the invention, a cell may be a control cell.

Imaging methods of the invention may be used in cells from culture, cells in solution, cells obtained from subjects, isolated cells, recombinant cells, and/or cells in a subject (in vivo cells). Imaging methods of the invention may be used in cultured cells, cultured tissues (e.g., brain slice preparations, organ preparations, etc.), and in living subjects, etc. As used herein, a the term "subject" may refer to a human, non-human primate, cow, horse, pig, sheep, goat, dog, cat, bird, rodent, insect, or other suitable vertebrate or invertebrate organism. In certain embodiments of the invention, a subject is a mammal and in certain embodiments of the invention a subject is a human.

Controls and Candidate Compound Testing and Screening

Processes and/or conditions in one or more cells may be imaged using embodiments of methods of the invention and methods of the invention can also be used to determine an alteration, activity, and/or change in process or condition in one or more imaged cells. Thus, some aspects of the invention provide methods of determining the presence or absence of one or more activities, alternations, changes or modulations in a cell. Some embodiments of the invention include using imaging methods of the invention to identify effects of candidate compounds on cells, tissues, and subjects. Results obtained by imaging a cell using a method of the invention can be advantageously compared to a control. In some embodiments of the invention imaging of one or more cells using a method of the invention may be performed in a cell or plurality of cells and used to test the effect of candidate compounds on the cell or plurality of cells. A "test" cell may be a cell in which the activity in the cell may be tested or assayed. Results obtained using assays and tests of a test cell using a method of the invention may be compared results obtained from the assays and tests performed in other test cells or assays and/or may be compared to a control value.

As used herein a control value may be a predetermined value, which can take a variety of forms. It can be a single cut-off value, such as a median or mean. It can be established based upon comparative groups, such as cells or tissues that have been imaged under similar conditions using a method of the invention, but are not contacted with a candidate compound with which the test cell is contacted and imaged. Another example of comparative groups may include cells or tissues that have a disorder or condition and groups without the disorder or condition. Another comparative group may be cells from a group with a family history of a disease or condition and cells from a group without such a family history. A predetermined value can be arranged, for example, where a tested population is divided equally (or unequally) into groups based on results of testing. Those skilled in the art are able to select appropriate control groups and values for use in comparative methods of the invention.

As a non-limiting example of use of method of the invention to assess the presence or absence of a change in a cell as a means to identify a candidate compound, the physiology and/or activity in a cell may be imaged using a method of the invention in culture or in a subject and the cell may then be contacted the candidate compound and re-imaged using a method of the invention. Any change in the physiology and/or activity of the imaged cell as determined using imaging methods of the invention, may indicate an effect of the candidate compound on the cell. In some embodiments of the invention, methods of the invention may be used to image the physiology and/or activity in one or more test cells before and after the one or more test cells is contacted with a candidate compound and the before and after imaging results can be compared to determine whether or not contact with the candidate compound resulted in a change in physiology and/or activity in the one or more test cells. In another embodiment of the invention, imaging of physiology and/or activity in one or more test cells using a method of the invention may be performed after contacting the one or more test cells with a candidate compound and the imaging results can be compared to control values for imaging of physiology and/or activity to determine whether or not a change in physiology and/or activity occurred in the one or more test cells.

A cell, tissue, and/or subject that include a cell imaged with a method of the invention may be monitored for the presence or absence of a change that occurs in the test conditions versus the control conditions. As a non-limiting example, in a cell, a change in the physiology and/or activity may include, but is not limited to a change in depolarization of the cell, a change in a depolarization-mediated cell characteristic, response to stimuli, an action potential, pH change, release of a neurotransmitter, etc. Art-known methods can be used to assess the effect of a physiology and/or cell activity as imaged using methods of the invention, with or without additional contact with a candidate compound.

STARC Imaging Compound Variants

STARC molecule and compound variants can be prepared and used in embodiments of methods of the invention. For example, although not intended to be limiting, STARC-GCaMP variants can be identified based on sequence similarity to the sequence of the STARC-GCaMP compound provided above herein. Additional variants of STARC molecules may also be identified, tested for function, and used in imaging methods of the invention according to procedures described herein. As used herein, the term "parent" when used in the context of a variant STARC molecule of the invention means the STARC molecule of which the variant STARC molecule is the variant. Based on the teaching provided herein regarding STARC molecules and compounds, functional variants of STARC molecules that have sufficient amino acid sequence similarity/identity to a parent STARC molecule sequence and have at least a portion of the function of the parent STARC molecule in methods of the invention, can be prepared and used in imaging methods of the invention.

As used herein, the term "identity" refers to the degree of relatedness or similarity between two or more polypeptide sequences [or polynucleotide (nucleic acid) sequences]. Sequence identify may be determined by the alignment and match between the sequences using standard methods. The percentage is obtained as the percentage of identical amino acids in two or more sequences taking account of gaps and other sequence features. The identity between polypeptide sequences can be determined by means of art-known procedures. Algorithms and programs are available and routinely used by those in the art to determine identity between polypeptide sequences and to determine identity between nucleic acid sequences. Non-limiting examples of programs and algorithms include BLASTP, BLASTN and FASTA (Altschul et al., NCB NLM NIH Bethesda Md. 20894; Altschul et al., 1990), Online BLAST programs from the National Library of Medicine are available, for example, at blast.ncbi.nlm.nih.gov/Blast.cgi.

The presence of functionality of a variant, for example the ability to be used in imaging methods of the invention, can be determined using assay and testing methods described herein. Functional variants of STARC compounds, including but not limited to functional variants of a STARC-GCaMP compound, can be used in imaging methods described herein. It will be understood that the level of sequence identity with a STARC-GCaMP compound or other STARC compound of the invention, and the level of functionality with respect to imaging, can be characteristics used to identify STARC-GCaMP variants and other STARC compounds using the teaching provided herein in conjunction with standard procedures for sequence alignment, comparisons, and knowledge of sequence modifications in the protein arts. A functional STARC molecule variant of the invention will have at least a portion of the functionality of the STARC molecule of which it is a variant. As used herein, the terms "functional" and "functionality" used in reference to a STARC variant means the ability to perform in imaging methods of the invention as described herein. A functional variant need not have an identical level of function as its parent STARC molecule, but will have at least a portion of the functionality of the parent STARC molecule and in some instances may have a level of function equivalent to, or higher than that of its parent STARC molecule when used in methods of the invention.

A variant of a STARC imaging compound, including but not limited to a STARC-GCaMP, may comprise a STARC polypeptide sequence such as a STARC-GCaMP polypeptide sequence, (and be encoded by a nucleic acid sequence)

with one or more sequence modifications. It will be understood that a modified binding polypeptide, a modified linker polypeptide and/or a modified indicator polypeptide may be referred to herein as a "modified STARC polypeptide". A modified STARC imaging compound may include at least one modification in one or more of: a binding polypeptide, a linker polypeptide, and an indicator polypeptide that are part of the STARC imaging compound. As used herein the term "modified" or "modification" in reference to a polypeptide sequence refers to a change such one or more of an insertion, deletion, or substitution of 1, 2, 3, 4, 5, 6, 7, 8, 9, 10, or more amino acids in the sequence as compared to the unmodified STARC sequence of the invention, a non-limiting example of which is the STARC-GCaMP sequence described herein. As an example, though not intended to be limiting, the amino acid sequence of a modified STARC-GCaMP polypeptide may be identical to the amino acid sequence described herein for STARC-GCaMP except that it has one or more amino acid substitutions, deletions, insertions, or combinations thereof. In some embodiments of the invention a modified STARC-GCaMP sequence may include of 1, 2, 3, 4, 5, 6, 7, 8, 9, 10, or more amino acid substitutions in a STARC-GCaMP polypeptide sequence of the invention.

The sequence of a STARC polypeptide can be modified with one or more substitutions, deletions, insertions, or other modifications and the resulting STARC polypeptide variant can be tested using methods described herein for characteristics including, but not limited to: expression, cell localization, imaging, etc. Exemplary modifications include, but are not limited to conservative amino acid substitutions, which will produce molecules having functional characteristics similar to those of the molecule from which such modifications are made. Conservative amino acid substitutions are substitutions that do not result in a significant change in the activity or tertiary structure of a selected polypeptide or protein. Such substitutions typically involve replacing a selected amino acid residue with a different residue having similar physico-chemical properties. For example, substitution of Glu for Asp is considered a conservative substitution because both are similarly sized, negatively charged amino acids. Groupings of amino acids by physico-chemical properties are known to those of skill in the art. The following groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). STARC variants, such as but not limited to a STARC-GCaMP variant, that include modifications such as, but not limited to one, two, three, four, or more conservative amino acid substitutions can be identified and tested for characteristics including, but not limited to: expression, cell localization, imaging characteristics, etc., using methods disclosed herein.

A STARC molecule variant may include modifications that result in an amino acid sequence having at least 80%, 85%, 90%, 95%, 96%, 97%, 98%, 99%, or 100% identity with the amino acid sequence of the STARC molecule of which it is a variant. For example, though not intended to be limiting, a STARC-GCaMP6f variant may include modifications from the parent STARC-GCaMP6f polypeptide such that the amino acid sequence of the variant has at least 80%, 85%, 90%, 95%, 96%, 97%, 98%, 99%, or 100% identity with the amino acid sequence of its parent STARC-GCaMP6f polypeptide. In addition, if assessing an individual STARC polypeptide such as an indicator polypeptide, a linker polypeptide, or a binding polypeptide that is a component of a STARC imaging compound, an indicator polypeptide variant, linker polypeptide variant, or binding polypeptide variant may include modifications that result in an amino acid sequence having at least 80%, 85%, 90%, 95%, 96%, 97%, 98%, 99%, or 100% identity with the amino acid sequence of the indicator polypeptide, linker polypeptide, or binding polypeptide, respectively, of which it is a variant. Sequence identity can be determined using standard techniques known in the art. In some embodiments of the invention, a STARC imaging compound variant may be shorter or longer than sequence of which it is a variant. A non-limiting example of types of changes that may be made in STARC polypeptides are changes in one more linker, indicator, and binding polypeptides. For example, a variant of the STARC-GCaMP6f polypeptide described herein as including: GCaMP6f, 12 amino acids which serve as a linker—GGSGGTGGSGGT (SEQ ID NO: 3), and 6 alternations between MVIBD and MBD as shown elsewhere herein, may have one or more of: a different activity reporter; one or more linker molecules that differ in length and/or sequence; one or more different binding repeat polypeptides; more or fewer MBD and/or MVIBD sequences; and a different number and/or arrangement of MBD and MVIBD sequences, etc. Different combinations of indicator polypeptides, linking polypeptides, and binding polypeptides are also envisioned in certain aspects of STARC imaging compounds and methods of the invention.

Another aspect of the invention provides nucleic acid sequences that code for a STARC imaging compound of the invention, a non-limiting example of which is a STARC-GCaMP6f compound or variants thereof. It would be understood by a person of skill in the art that STARC polypeptides of the invention variants thereof, can be encoded (coded for) by various nucleic acids. Each amino acid in the protein is represented by one or more sets of three nucleic acids (codons). Because many amino acids are represented by more than one codon, there is not a unique nucleic acid sequence that codes for a given protein. It is well understood by those of skill in the art how to make a nucleic acid that can encode a polypeptide when the amino acid sequence of the polypeptide is known. A nucleic acid sequence that codes for a polypeptide or protein is the "gene" of that polypeptide or protein. A gene can be RNA, DNA, or other polynucleotide than will code for the polypeptide or protein. As used herein the term "nucleic acid" is used interchangeably with the term "polynucleotide".

It is understood in the art that the codon systems in different organisms can be slightly different, and that therefore where the expression of a given protein from a given organism is desired, the nucleic acid sequence can be modified for expression within that organism. Thus, in some embodiments, a STARC polypeptide of the invention, a non-limiting example of which is a STARC-GCaMP6f polypeptide or variant thereof, is encoded by a mammalian-codon-optimized nucleic acid sequence, which may in some embodiments be a human-codon optimized nucleic acid sequence. An aspect of the invention provides a nucleic acid sequence that codes for a STARC polypeptide or variant thereof, such as a STARC-GCaMP6f or variant thereof, that is optimized for expression with a mammalian cell. In some embodiments of the invention, a nucleic acid that encodes a STARC polypeptide or variant thereof includes a nucleic acid sequence optimized for expression in a human cell.

Delivery of STARC Imaging Polypeptides and Variants

Delivery of a STARC imaging polypeptide, including but not limited to STARC-GCaMP6f polypeptides and or variants thereof, to a cell and/or expression of a STARC imaging polypeptide or variant thereof in a cell can be done using art-known delivery means. In some embodiments of the invention a STARC imaging polypeptide or variant thereof is included in a fusion protein. It is well known in the art how to prepare and utilize fusion proteins that comprise a polypeptide sequence. In certain embodiments of the invention, a fusion protein can be used to deliver a STARC imaging polypeptide, or variant thereof to a cell and can also in some embodiments be used to target a STARC imaging polypeptide, or variant thereof of the invention to specific cells or to specific cells, tissues, or regions in a subject. Targeting and suitable targeting sequences for delivery to, and expression in, a desired cell, tissue or region can be performed using art-known procedures.

It is an aspect of the invention to provide a STARC compound of the invention, such as, but not limited to a STARC-GCaMP6f polypeptide or variant thereof that is non-toxic, or substantially non-toxic in cells in which it is expressed. Compositions of the invention may comprise a STARC imaging compound that includes an indicator polypeptide, linking polypeptide, and binding polypeptides. Such compositions may be used in aspects of imaging methods of the invention. In some embodiments of the invention, a STARC imaging polypeptide or variant thereof is genetically introduced into a cell and/or cellular membrane and reagents and methods are provided for genetically targeted expression of a STARC imaging polypeptide or variant thereof. Genetic targeting can be used to deliver a STARC imaging polypeptide or variant thereof of the invention to one or more of: specific cell types, specific cell subtypes, specific spatial regions within an organism, and sub-cellular regions within a cell. Genetic targeting also relates to the control of the amount of a STARC imaging polypeptide or variant thereof that is expressed, and the timing of the expression.

Some embodiments of the invention include a reagent for genetically targeted expression of a STARC imaging polypeptide or variant thereof, wherein the reagent comprises a vector that contains the gene for the STARC imaging polypeptide or a variant thereof. As used herein, the term "vector" refers to a nucleic acid molecule capable of transporting between different genetic environments another nucleic acid to which it has been operatively linked. The term "vector" also refers to a virus or organism that is capable of transporting the nucleic acid molecule. One type of vector is an episome, i.e., a nucleic acid molecule capable of extra-chromosomal replication. Some useful vectors are those capable of autonomous replication and/or expression of nucleic acids to which they are linked. Vectors capable of directing the expression of genes to which they are operatively linked are referred to herein as "expression vectors". Other useful vectors, include, but are not limited to viruses such as lentiviruses, retroviruses, adenoviruses, and phages. Vectors useful in some methods of the invention can genetically insert a STARC imaging polypeptide or variant thereof into dividing and non-dividing cells and can insert a STARC imaging polypeptide, or variant thereof to cells that are in vivo, in vitro, or ex vivo cells.

In certain embodiments of the invention, function of a variant of a STARC molecule can be tested by cloning the gene encoding the altered polypeptide into a bacterial or mammalian expression vector, introducing the vector into an appropriate host cell, expressing the altered polypeptide, and testing for a functional capability of the polypeptide as disclosed herein. Additional methods for generating fusion proteins and recombinant polypeptides are known in the art may include use of prokaryotic and eukaryotic expression systems including but not limited to bacterial and mammalian expression systems.

Vectors useful in methods of the invention may include additional sequences including, but not limited to one or more signal sequences and/or promoter sequences, or a combination thereof. Expression vectors and methods of their use are well known in the art. Non-limiting examples of suitable expression vectors and methods for their use are provided herein. In certain embodiments of the invention, a vector may be a lentivirus comprising the gene for a STARC imaging polypeptide or variant thereof. A lentivirus is a non-limiting example of a vector that may be used to create stable cell line. The term "cell line" as used herein is an established cell culture that will continue to proliferate given the appropriate medium.

Promoters that may be used in methods and vectors of the invention include, but are not limited to, cell-specific promoters or general promoters. Methods for selecting and using cell-specific promoters and general promoters are well known in the art. A non-limiting example of a general purpose promoter that allows expression of a STARC imaging polypeptide or variant thereof in a wide variety of cell types—thus a promoter for a gene that is widely expressed in a variety of cell types, for example a "housekeeping gene" can be used to express a STARC polypeptide, or variant thereof in a variety of cell types. Non-limiting examples of general promoters are provided elsewhere herein and suitable alternative promoters are well known in the art.

The present invention in some aspects includes one or more methods of preparing and using STARC polypeptide-encoding nucleic acid sequences; expressing in cells and membranes polypeptides encoded by the prepared nucleic acid sequences; and using the expressed polypeptides to image activity and/or physiology within the cell. The present invention enables imaging biological systems with high speed and nanoscale precision and the STARC polypeptides and polynucleotides of the invention and their use, have broad-ranging applications for drug screening, treatments, and research applications, some of which are describe herein.

Additional STARC Imaging Methods

Methods of the invention, in some aspects include methods of using a genetically encoded activity reporter (STARC imaging molecule) to assess one or more of an activity, alteration, process, condition or other physiological characteristic of a cell in which the STARC imaging molecule is expressed. In certain aspects, methods of the invention may include methods to assess an activity, process, or condition in a cell. In some aspects of the invention, methods may include: a genetically encoded activity reporter of the invention in a cell. The genetically encoded activity reporter will comprise two or more binding repeat polypeptides that self-polymerize when expressed, an indicator polypeptide, and a linker polypeptide. The cell is then imaged and the imaging permits an assessment of a process or condition in the cell, based at least in part on the imaging of the indicator polypeptide of the genetically encoded activity reporter in the cell. Thus, if it is of interest to assess calcium levels or changes in a cell, a STARC imaging molecule of the invention, a non-limiting example of which is STARC-GCaMP6f polypeptide or variant thereof, may be expressed in a cell and imaging performed to detect the fluorescence of the indicator in response to calcium in the cell.

Certain aspects of the invention also permit use of STARC imaging compounds of the invention to assess an effect of candidate agent on a process, activity, or condition in a cell. In such methods a STARC imaging compound may be expressed in a cell, wherein the STARC imaging compound includes two or more binding repeat polypeptides that self-polymerize when expressed, an indicator polypeptide, and a linker polypeptide. The expressed STARC imaging polypeptide can then be contacted with a candidate agent; and the cell can be imaged using methods of the invention to assess one or more of a process, condition, or activity in the cell, based at least in part on the imaging. The results of the imaging can be compared to a control assessment of the process, activity, or condition; and if there is a difference between the process or condition in the cell as assessed in the cell as compared to the control assessment of the process, activity, or condition it indicates that the candidate compound modulated or changed one or more of the process, activity, and condition in the cell. In some aspects of the invention the control assessment is an assessment in a cell in which the same type of STARC imaging polypeptide is expressed but that was not contacted with the candidate compound.

EXAMPLES

Example 1

Methods
  Molecular Cloning of STARC-GCaMP:
  All genes were optimized and synthesized using mammalian codon usage. The gene of the genetically encoded calcium indicator (GECI) GCaMP6f was fused with myosin binding repeats arrayed in tandem, the myosin binding repeats were for myosin 5a (MBD, SEQ ID NO:1) and myosin 6 (MVIBD, SEQ ID NO:2. The resulting genes contained GCaMP6f, 12 amino acids which serve as a linker—ggsggtggsggt (SEQ ID NO:3), and 6 alternations between MVIBD and MBD: GCaMP6F-12-MVIBD-MBD-MVIBD-MBD-MVIBD-MBD. This gene was dubbed STARC-GCaMP6f, and was subcloned either into an FCK plasmid under the CaMKII promoter, into a pLV vector under a CAG or Synapsin promoter, or into a pAAV plasmid under a CAG or synapsin promoter.
Primary Neuron Culture and Transfection and Transduction
  All procedures involving animals were in accordance with the National Institutes of Health Guide for the care and use of laboratory animals and approved by the Massachusetts Institute of Technology Animal Care and Use Committee. Swiss Webster or C57 mice (Taconic or Jackson Labs) were used. For hippocampal cultures, hippocampal regions of postnatal day 0 or day 1 mice were isolated and digested with 50 units of papain (Worthington Biochem) for 5 min, and the digestion was stopped with ovomucoid trypsin inhibitor (Worthington Biochem). Tissue was then mechanically dissociated with Pasteur pipettes, and centrifuged at 1000 rpm at 4° C. for 10 min. Dissociated neurons were plated at a density of approximately four hippocampi per 20 glass coverslips, coated with Matrigel (BD Biosciences). For cortical cultures, dissociated mouse cortical neurons (postnatal day 0 or 1) were prepared as previously described, and plated at a density of 20K per glass coverslip coated with Matrigel (BD Biosciences). Cultures were maintained in Neurobasal Medium supplemented with B27 (Invitrogen) and glutamine.
  Cultured neurons were transfected at 4 days in vitro (DIV) with a commercial calcium phosphate kit (Invitrogen). An additional washing with acidic MEM buffer (pH 6.8-6.9) was added after calcium phosphate precipitate incubation to completely resuspend residual precipitates. mCherry was sometimes used as a cotransfectant DNA reagent to assist with unbiased selection of STARC-GCaMP6f-expressing neurons; in this condition, condition, 0.1-2 μg of STARC-GCaMP6f DNA and 0.1-2 μg mCherry were delivered. Alternatively, neurons were infected with 0.1-1 μl of lentivirus or adeno-associated virus per well at 3-5 days in vitro.
Cultured Cells Preparation and Staining:
  All solutions are made up in 1×PBS, and incubations carried out at room temperature unless otherwise noted. Hippocampal neurons were fixed in 3% formaldehyde/0.1% glutaraldehyde (Electron Microscopy Sciences) for 10 minutes, followed by quenching in 100 mM glycine for 10 minutes and reduction with 0.1% NaBH$_4$ for 7 minutes. Cells were permeabilized with 0.2% Triton for 15 minutes at room temperature and blocked with 5% normal donkey serum for one hour. Specimens were incubated with primary antibodies in blocking buffer at a concentration of 10 μg/mL for 1-4 hours, and then washed in PBS three times for 5 minutes each. Specimens were incubated with DNA-labeled secondary antibodies in DNA hybridization buffer (2×SSC buffer, 10% Dextran sulfate, 1 mg/mL yeast tRNA, 5% normal donkey serum) at a concentration of approximately 10 μg/mL for 1-4 hours, then washed in PBS as for primary. Specimens were incubated with dye-labeled DNA tertiaries in hybridization buffer at a concentration of 0.5 ng/μL overnight, then washed three times in 2×SSC.
Tissue Preparation and Staining:
  Thy1-YFP-expressing mice were anesthetized with isoflurane and perfused transcardially with ice cold 4% paraformaldehyde. Brains were dissected out, left in 4% paraformaldehyde at 4° C. for one day, and then sunk in 30% sucrose with 100 mM glycine for one day. Tissue was frozen in −40° C. isopentane cooled with dry ice, embedded in M-1 embedding matrix (Thermo Scientific) and sliced on a cryotome. Slices were permeabilized and blocked in 1×PBS with 0.1% Triton and 2% normal donkey serum (slice blocking buffer) for at least six hours. Slices were incubated with primary antibodies in slice blocking buffer at a concentration of 10 μg/mL for 6-12 hours, and then washed in slice blocking buffer four times for thirty minutes each wash. Slices were incubated with DNA-labeled secondary antibodies in hybridization buffer at a concentration of approximately 10 μg/mL for 6-12 hours, then washed in slice blocking buffer as for primary. Specimens were incubated with dye-labeled DNA tertiaries in hybridization buffer at a concentration of 1 ng/μL for 6-12 hours, then washed in slice blocking buffer as for primary.
Hydrogel Embedding:
  Monomer solution (1×PBS, 2M NaCl, 8.625% (w/w) sodium acrylate, 2.5% (w/w) acrylamide, 0.15% (w/w) N,N'-Methylenebisacrylamide was mixed fresh every week. Prior to embedding, monomer solution was cooled to 4° C. to prevent pre-mature gelation. Concentrated stocks (10% w/v) of ammonium persulfate (APS) initiator and tetramethylethylenediamine (TEMED) accelerator were added to the monomer solution up to 0.2% (w/w) each. Stained cells or tissue slices were incubated with the monomer solution plus APS/TEMED at 4° C. for two minutes (cultured cells) or ten minutes (slices), and then transferred to a 37° C. oven for one hour.
Digestion and Expansion:
  Proteinase K (New England Biolabs) was diluted to 200 μg/mL in digestion buffer (50 mM Tris pH8, 1 mM EDTA, 0.5% Triton-X100, 1M NaCl, 0.8M guanidine HCl) and applied directly to gels in at least ten times volume excess. In certain studies gels were formed in a Culturewell Chambered Coverglass (Invitrogen), and the chamber walls removed before adding digestion buffer in order to improve access of enzyme to the embedded tissue. The gels were then incubated in digestion buffer for greater than 6 hours to ensure complete digestion of all proteins. Digested gels were next placed in excess volume of doubly de-ionized or distilled water for several hours to expand. This step was repeated several times to ensure the gel reached equilibrium. The expanded gels were imaged on a standard optical microscope, though high light gathering and detector sensitivity were useful in imaging due to the volumetric dilution of bound dye molecules.

Imaging:

Widefield imaging was performed using a Leica 3000B microscope, using a 40×PL FLUO, 0.6 NA lens, and under blue light illumination from X-Cite® XLED1 lightsource (Excelitas Technologies Corp.). Imaging was performed using a Digital CMOS camera ORCA-Flash4.0 (Hamamatsu), at 10 Hz or 50 Hz. Widefield imaging was also performed with a Nikon Eclipse Ti microscope, using the same lens as described above, and under blue light illumination from Spectra X light engine (Lumencore). Imaging was performed using a Zyla 5.5 sCMOS camera (Andor) at 10 Hz.

Results/Discussion

STARC Characteristics

Studies were performed that demonstrated stochastic arrangement of reagents in clusters using STARC methods of the invention. Results obtained in studies using standard optical sensor methods were compared to results obtained using STARC methods, which included sensors arranged into clusters and spaced at least a diffraction limited distance apart. The top row of FIG. 1A illustrates that imaging optical sensors expressed in the in vivo brain (left) result in an image where parts of different cells could not be resolved because they make contacts within a diffraction limited space due to the compact architecture of the brain (right). The STARC results demonstrated the improved imaging as a result of the STARC methods.

Optical reagents were utilized using described experimental methods to arrange the optical reagents into clusters that were spaced at least a diffraction-limited distance apart. The bottom row of FIG. 1A illustrates that to enable imaging of multiple neurons (left panel) with subcellular resolution, optical reagents were arranged into clusters that were spaced at least a diffraction limited distance apart (middle panel). The clusters were subsequently associated with cells via super-resolution imaging (right panel).

Figure 1B:
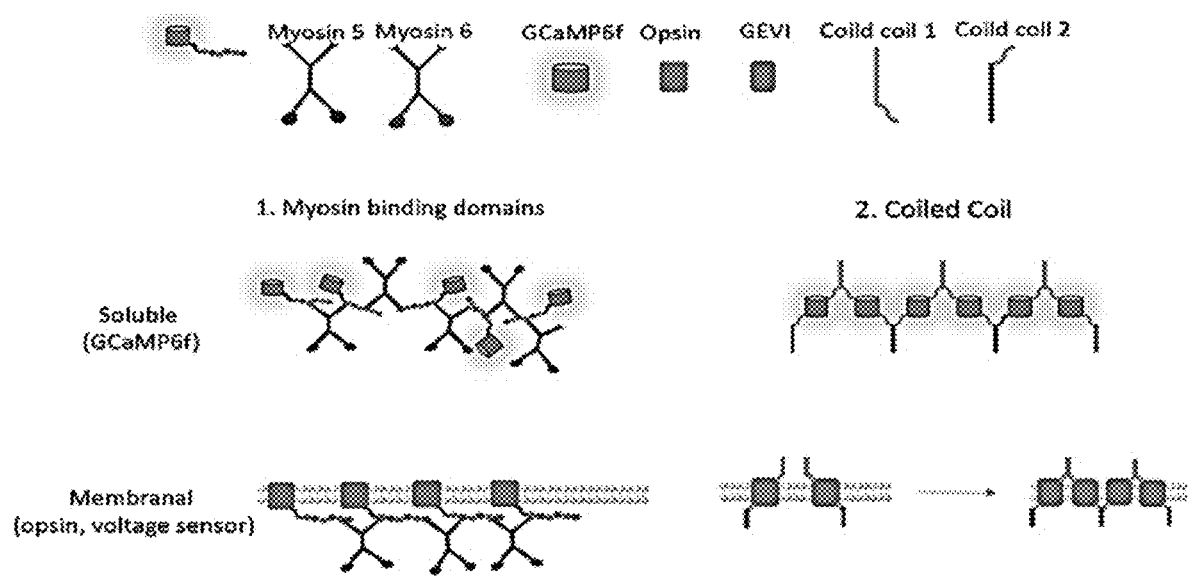

Experiments were performed with STARC methods and FIG. 1B illustrates molecular strategies used to achieve STARC. FIG. 1B, left panel shows fusing optogenetic tools (in a non-limiting example, GCaMPGf is illustrated) with myosin 6 and 5 tandem repeats. The myosin repeats lead to clustering of their cargos across neurites in the cell. The right panel of FIG. 1B shows process of coiled-coil induced clustering of genetically encoded sensors. In experiments, homo-oligomerizing coiled-coils were fused to the N and C termini of sensors and resulted in clustering of the sensors. Results of the studies indicated that although the clustering of cytosolic sensors was induced in the cytoplasm, genetically encoded voltage sensors formed clusters in the membrane.

Figure 2A:
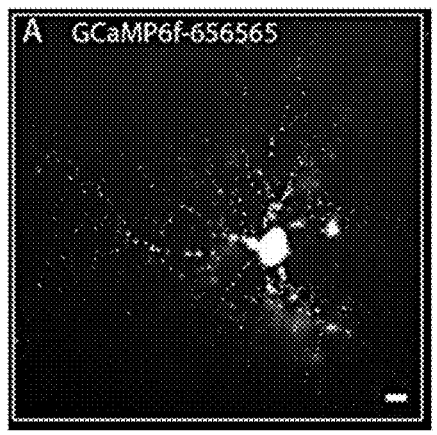
FIG. 2A-I provides photomicroscopic images, graphs, and recording images of results of analysis of one cell using embodiments of methods of the invention. The figure shows characteristics of STARC-GCaMP6f in a cultured mouse Hippocampal Neuron.
Figure 2B:
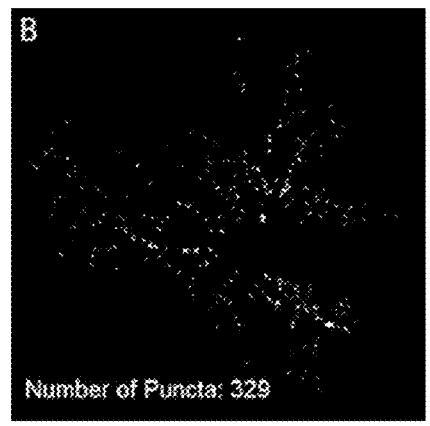
Figure 2C:
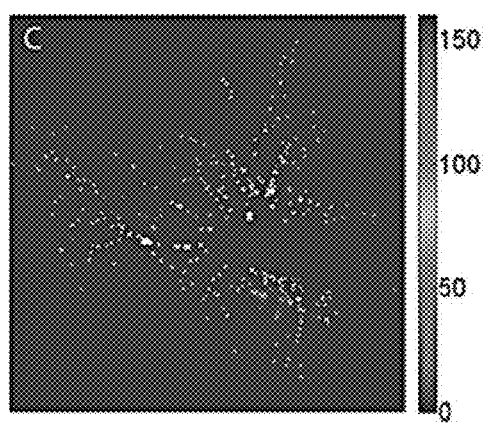

Additional studies of STARC methods and compounds were performed in single cells. FIG. 2A-I shows results of analyses preformed on one cell and shows characteristics of STARC-GCaMPGf in a cultured mouse Hippocampal Neuron. FIG. 2A is a photomicrograph of a wide-field image of cultured hippocampal neurons expressing STARC-GCaMP6f. The analyzed area denoted by the rectangle shown within the image. FIG. 2B is a photomicrograph of a binary image with somatic clusters removed. FIG. 2C is a photomicrograph of a df/f map showing field of view with color-coded response of each cluster. The hue denotes the maximum response ($\Delta F_{max}/F$) recorded from a cluster during the 100 s time increment.

Figure 2D:
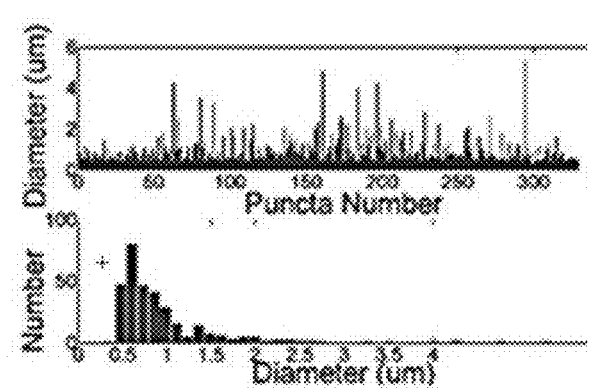
Figure 2E:
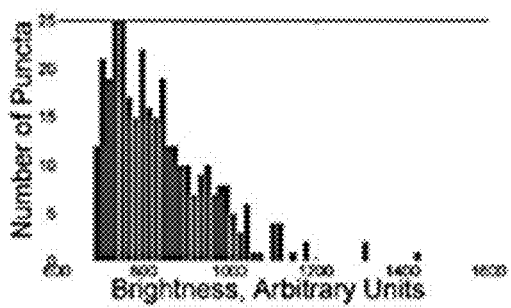
Figure 2F:
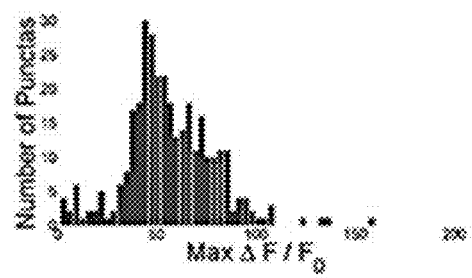
Figure 2G:
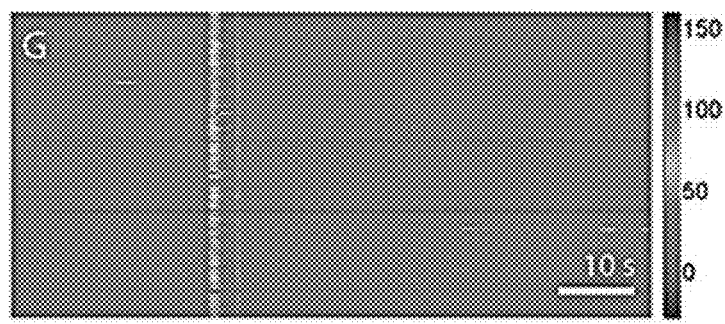
Figure 2H:
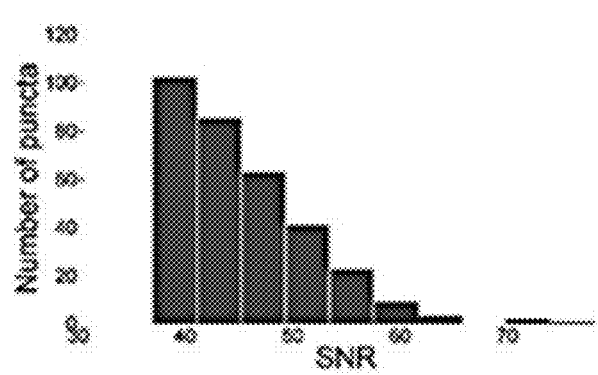
Figure 2I:
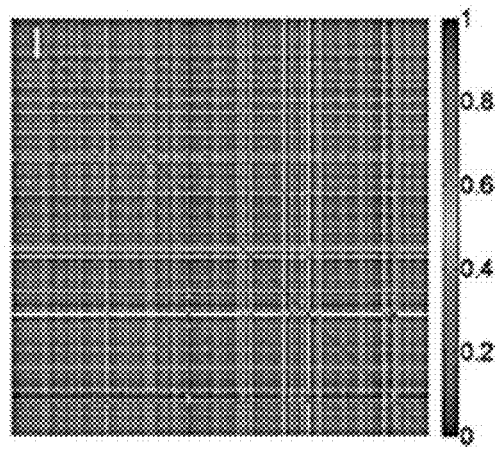

Studies of characteristics of the clusters included examination of the diameter, number, and size distribution of the clusters. Results are illustrated in FIG. 2D. The top graph of FIG. 2D shows the diameter (size) of each cluster and the bottom graph of FIG. 2D shows the size distribution of clusters in the field of view. FIG. 2E is a brightness histogram of clusters with brightness given in arbitrary units. FIG. 2F is a maximum response ($\Delta F_{max}/F$) cluster histogram. FIG. 2G shows results obtained in a single-trial time-response of clusters. Each row shows the-time response of a cluster with the color hue denoting percent fluorescence change ($\Delta F/F$). FIG. 2H is a graph showing signal-to-noise ratio distribution among clusters. The signal-to-noise ratio was calculated as amplitude/1× standard deviation of signal. FIG. 2I is a graph showing the Matrix of Correlation values between clusters. Color denotes the degree of correlation (Pearson's R) between any two clusters. Scaling is indicated on the right.

Overall, results of the studies demonstrated successful application of STARC methods and analysis and confirmed that imaging obtained through use of STARC methods of the invention was greatly improved compared to imaging obtained using prior optical imaging methods.

Example 2

Figure 3A:
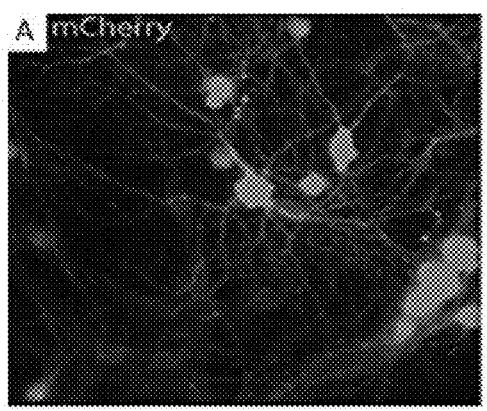
FIG. 3A-I shows photomicroscopic images demonstrating stochastic arrangement of reagents in clusters-STARC.
Figure 3B:
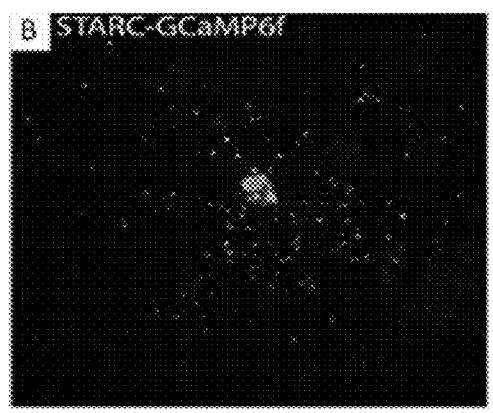
Figure 3C:
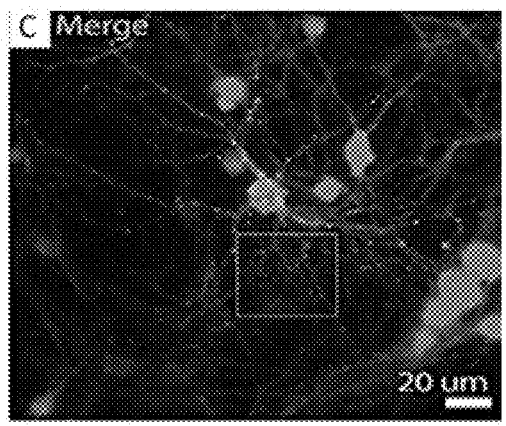

Myosin Binding Repeats Create Discrete, Diffraction-Limited Bright GCaMP6f Puncta that Respond to Physiological Stimulus To create discrete puncta of GCaMP6f, repeats of N-terminal fusions of GCaMP6f with different combination and repeats of myosin 6 binding repeat (MVIBD) and myosin5a binding repeat (MBD) were tested. Methods included those disclosed herein and in Example 1. Results indicated that one of the variants, GCaMP6f-MVIBD-MBD-MVIBD-MBD-MVIBD-MBD produced puncta that were bright and responsive to physiological stimuli. The protein was termed: "STARC-GCaMP6f". These puncta were round (FIG. 3A), cytosolic (FIG. 3E-I) and filled the entire cell (FIG. 3C). Addition experiments were performed to test different combinations of components of a genetically encoded activity reports. Other combinations included GCaMP6f fused to different combinations of the myosin binding repeat. No construct that contain MBD upstream of MVIBD expressed. Constructs that contained one repetition of MVIBD-MBD were not clustered but expressed in the soma; constructs which contained two repetitions: MVIBD-MBD-MVIBD-MBD, formed smaller clusters than STARC-GCaMP6f and constructs that included more than three repetitions: MVIBD-MBD-MVIBD-MBD-MVIBD-MBD-MVIBD-MBD, formed bigger clusters than STARC-GCaMP6f.

Figure 3D:
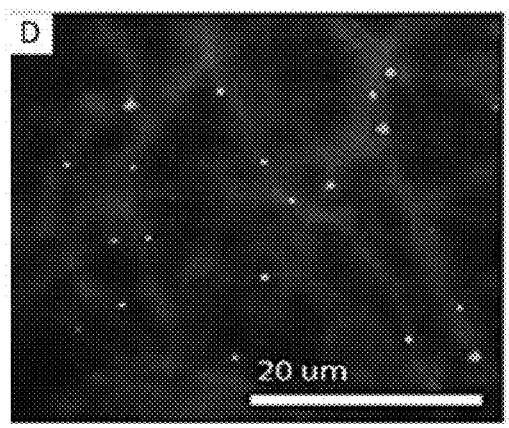
Figure 3E:
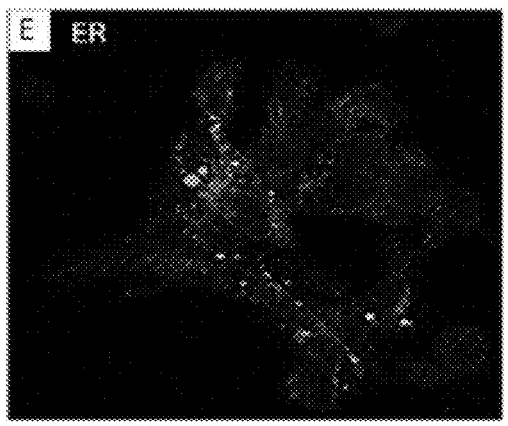
Figure 3F:
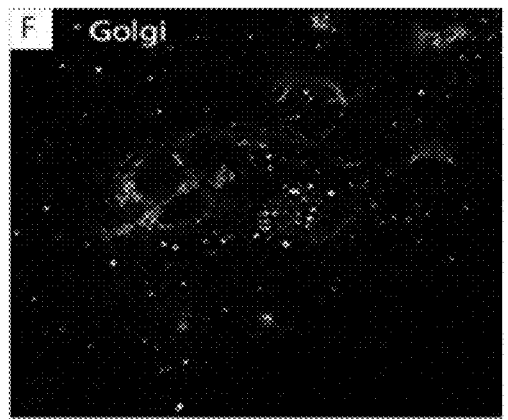
Figure 3G:
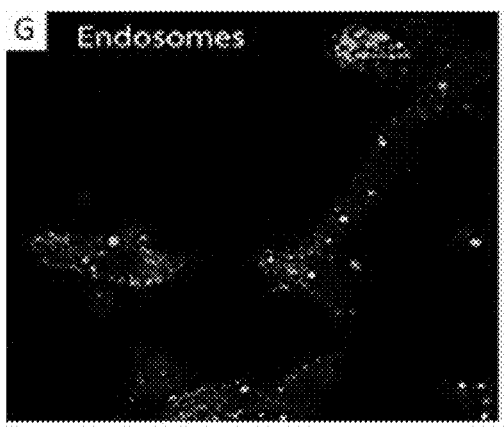
Figure 3H:
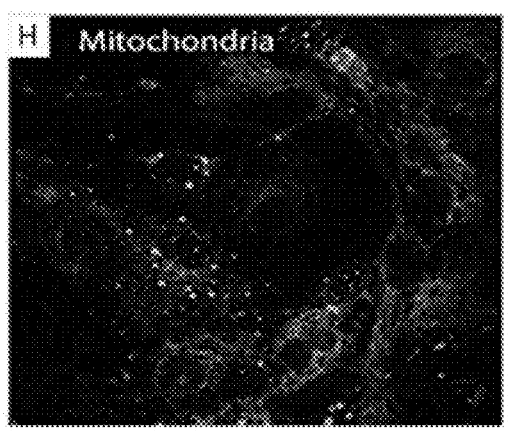
Figure 3I:
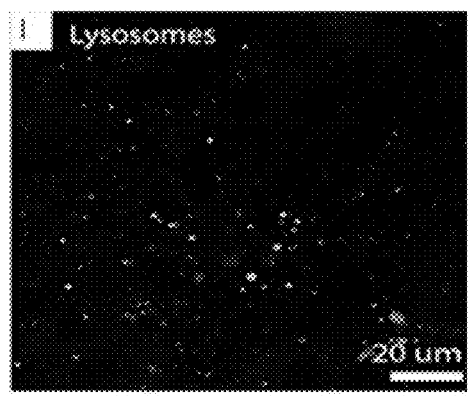

Studies were performed to examine stochastic arrangement of reagents in clusters (STARC) molecules and methods. Primary hippocampal neurons were cultured and transfected with mCherry and STARC-GCaMP6f and imaging results are shown in FIG. 3B and FIG. 3C, respectively. The images of FIGS. 3A and 3B were merged and results shown in FIG. 3C. FIG. 3D provides with a zoom image of the inset shown in FIG. 3C. The experimental cells were subsequently fixed, and immunostaining was performed against a set of organellar proteins. Lysosomes were stained using LysoTracker on live cells followed by fixation. After fixation, native STARC-GCamp6F fluorescence was imaged with a confocal microscope. Immunostaining against protein disulfide isomerase (PDI) was performed to visualize the endoplasmic reticulum. Immunostaining against Receptor binding cancer antigen expressed on SiSo cells (RCAS1) was carried out to visualize the Golgi apparatus. Immunostaining against early endosome antigen 1 (EEA1) was performed to visualize early endosomes. Immunostaining against apoptosis-inducing factor (AIF) was carried out to visualize mitochondria. Lysosomes were visualized using LysoTracker Red DND-99. All immunostaining was performed using standard methods. Results of the immunostaining are shown in FIG. 3E-I.

Immunostaining was performed as follows: specimens were stained with rabbit monoclonal antibodies against PDI, RCAS1, AIF, EEA1, and LAMP1 using the Organelle localization IF antibody sampler kit (#8653) from Cell Signaling Technology using the manufacturer's protocol. Briefly, specimens were blocked for 1 hr at room temperature using the blocking buffer recommended by the protocol. Specimens were incubated with antibodies overnight at 4° C. in the provided antibody dilution buffer. After performing washes with 1×PBS, a goat anti-rabbit secondary antibody conjugated to DyLight 650 (Pierce, SA5-10034) was diluted into the recommended antibody dilution buffer to a final concentration of 5 μg/ml. The fixed specimens were incubated with the secondary antibody for 2 hours at room temperature and subsequently washed with 1×PBS.

Example 3

STARC-GCaMP6f Forms Puncta that are Similar in Brightness, Sensitivity and Speed to GCamp6f Studies were performed to assess characteristics such of puncta formed by expression of STARC-GCaMP6f and to compare the characteristics with those of expressed GCaMP6 without STARC. Methods are as described herein with additional methods as disclosed in Examples 1 and 2.

Figure 4A:
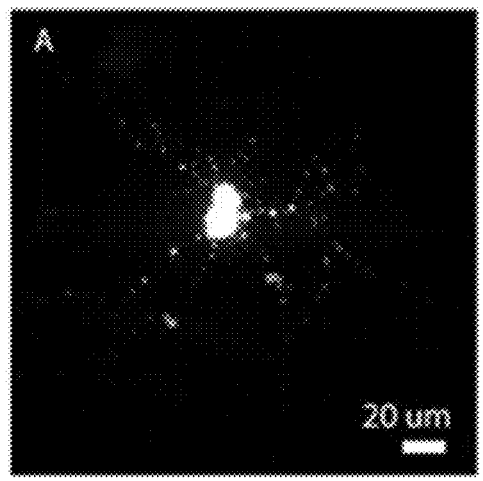
FIG. 4A-N shows photomicrographic images, graphs, and plots demonstrating that STARC-Gcamp6f puncta report physiological events while maintaining sensitivity, speed and brightness of GCaMP6f.
Figure 4B:
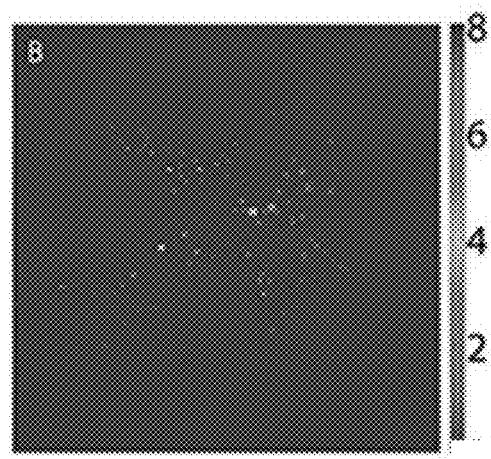
FIG. 4B is a df/f map showing field of view with color-coded response of each cluster.
Figure 4C:
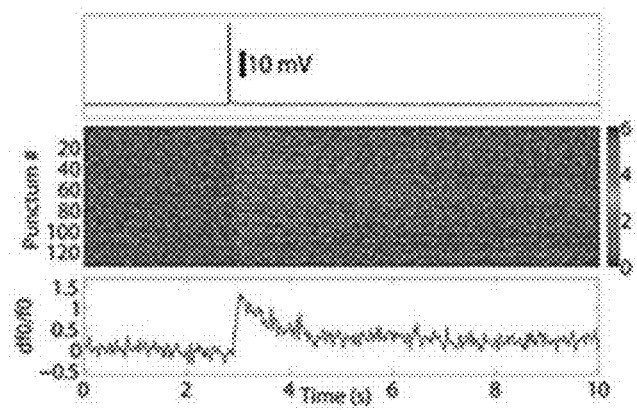
FIG. 4C, (top panel) shows electrophysiological recording from the cell showing 1 AP.
Figure 4D:
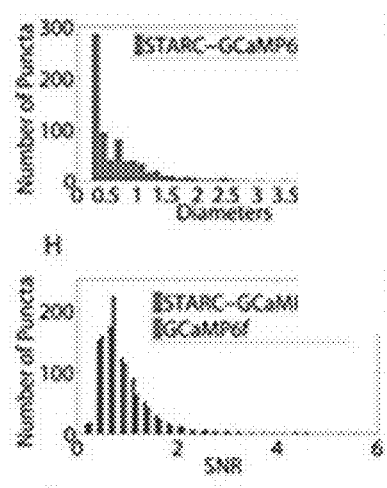
FIG. 4D shows size distribution of clusters in field of view.

Analysis of the puncta revealed that they range in diameter between 0.2 μm-2 μm. The distance between any two puncta fell between 0.4-20 μm, whereas 94% fell within 0.4-10 μm (FIG. 4D, n=5 cells, 908 puncta). STARC-GCamP6f had an average brightness of 450±13 AU and was found to be significantly brighter than GCaMP6f which had an average brightness of 439±18 AU (KS test, FIG. 4F, n=5 cells in STARC-GCamP6f and GCamP6f, number of puncta=908). This could be an effect of concentrating the sensor in single spots. Analysis was performed of the response of STARC-GCamP6f to an action potential. Following an action potential 99% of the puncta within the field of view responded with a df/f0>1% (FIG. 3B). It was found that STARC-GCaMP6f has similar sensitivity to that of GCaMP6f (FIG. 4G), with the responses ranging between 1-12% for both (n=5 cells in STARC-GCamP6f and GCamP6f, number of puncta=908) for an action potential. In addition the signal to noise ratio (SNR) was similar in both STARC-GCamP6f and GCamP6f, and ranged between 0.1-5 for a single action potential (FIG. 4G, n=5 cells in STARC-GCamP6f and GCamP6f, number of puncta=908). Temporally, the response rise-time (Ton) was similar and insignificantly different for STARC-GCamP6f and GCamP6f at 79.8+9.8 ins and 97.7±8.5 respectively (FIG. 4I). The response decay times (Toff) were also similar and insignificantly different between STARC-GCamP6f and GCamP6f at 835±212 ms and 685±113 ms respectively (FIG. 4J). Another parameter we measured was the ratio between df/f at the spot, and df/f in between spots (Signal-to-background) ratio. It was found that the average SNB was 11±14 and ranged between 1 and 60 (n=5 cells in STARC-GCamP6f and GCamP6f, number of puncta=908). When allowed to spike spontaneously, the puncta blinked with a df/f0 of up to 150-200% (FIG. 4 L-N).

Figure 4L:
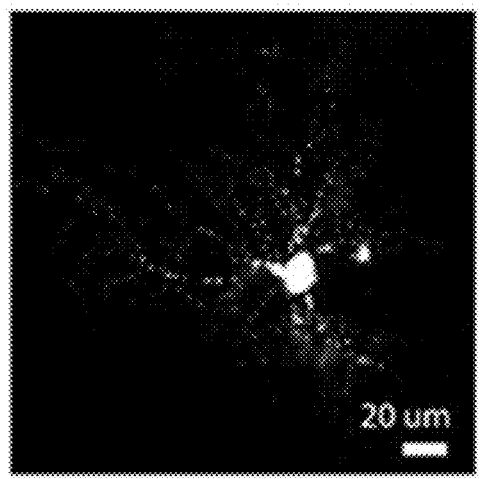
FIG. 4L provides a wide-field Image of a cultured hippocampal neuron expressing STARC-GCamp6f.
Figure 4M:
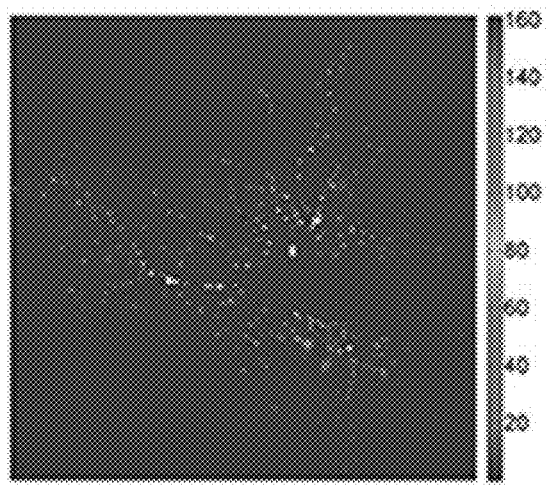
FIG. 4M shows a df/f map showing field of view with color-coded response of each cluster during a 50 s time period.
Figure 4N:
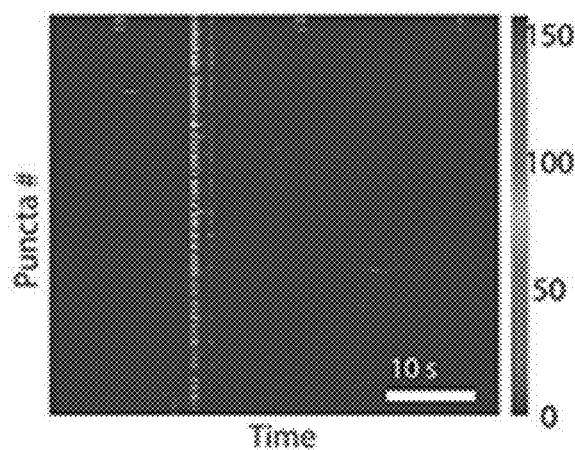

Studies were performed to assess reporting of STARC-GCaMP6f puncta. Results demonstrated that STARC-GCamp6f puncta report physiological events while maintaining sensitivity, speed and brightness of GCaMP6f. Electrophysiological studies were carried out to characterize STARC-GCaMP6f during 1 action potential. FIG. 4A is a wide-field Image of a cultured hippocampal neuron expressing STARC-GCaMP6f. FIG. 4B is a df/f map showing field of view with responses of each cluster. The image denotes the maximum response ($\Delta F_{max}/F0$) recorded from a cluster during the action potential (AP). FIG. 4C, (top panel) shows electrophysiological recording from the cell showing one AP. The time response of all of the STARC clusters was examined and FIG. 4C, middle panel, shows time-response of all clusters. Each row shows the time response of a cluster with the color hue denoting percent fluorescence change ($\Delta F/F0$). FIG. 4C, bottom panel shows the average time response of all clusters in the cell. F Additional studies were performed to further characterize STARC-GCaMP6f and to compare characteristics and function of STARC-GCaMP6f and GCaMP6f. FIG. 4D shows size distribution of clusters in field of view. FIG. 4E shows the distribution of nearest neighbor distances of clusters. FIG. 4F shows brightness histograms in STARC-GCaMP6 cells and control cells. To assess brightness, Kolmogorov-Smirnov (KS) tests were conducted using standard methods and results indicated that STARC-GCaMP6f was significantly brighter than GCaMP6f (KS test: alpha=1, n=908, $p=6.6330 \times 10^{-90}$). FIG. 4G shows the maximum response to one action potential ($\Delta F_{max}/F$) histogram for STARC-GCaMP6f clusters and GCaMP6f. No significant differences between populations were found (KS test: alpha=0, n=908, p=0.3347). FIG. 4H shows a Signal-to-Noise ratio (SNR) distribution among STARC-GCaMP6f clusters and GCaMP6f clusters. No significant differences between distributions were found (KS test: alpha=0, n=908, p=0.0983). FIG. 4I shows fluorescence rise time (Ton) of STARC-GCaMP6f and GCaMP6f. No significant difference of Ton was observed between STARC-GCaMP6f and GCaMP6f. (ANOVA: alpha=0.05, n=5, p=0.2098). FIG. 4J shows fluorescence decay time (Toff) of STARC-GCaMP6f and GCaMP6f. No significant difference of Toff was observed between STARC-GCaMP6f and GCaMP6f. (ANOVA: alpha=0.05, n=5, p=0.55). FIG. 4K shows signal to background distribution for 100 clusters, from 4 different cells for 1 action potential. FIG. 4L-N illustrates results of studies characterizing STARC-GCaMP6f during spontaneous activity. FIG. 4L provides a wide-field Image of a cultured hippocampal neuron expressing STARC-GCamp6f. FIG. 4M shows a df/f map showing field of view with color-coded response of each cluster during a 50 s time period. The hue denotes the maximum response ($\Delta F_{max}/F0$) recorded from a cluster during the time period. FIG. 4N shows the time-response of all clusters. Each row shows the time response of a cluster with the color hue denoting percent fluorescence change ($\Delta F/F0$).

Example 4

Sub-Cellular Physiological Imaging Using STARC-GCaMP6f and Expansion Microscopy

Figure 5A:
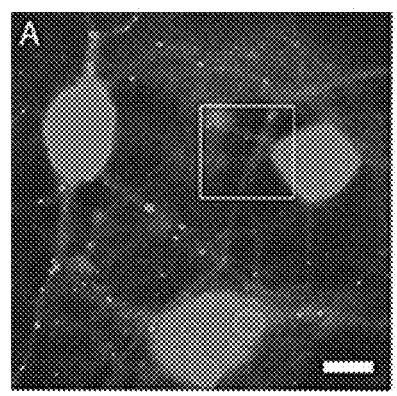
FIG. 5A-E shows photomicrographic images and a plot indicating that STARC-GCaMP6f permits unambiguous attribution of neural activity within dense networks of neural processes in vitro.
Figure 5B:
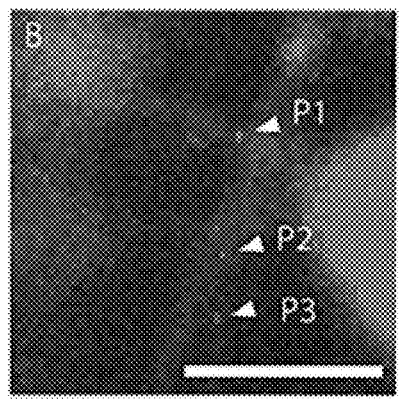
Figure 5C:
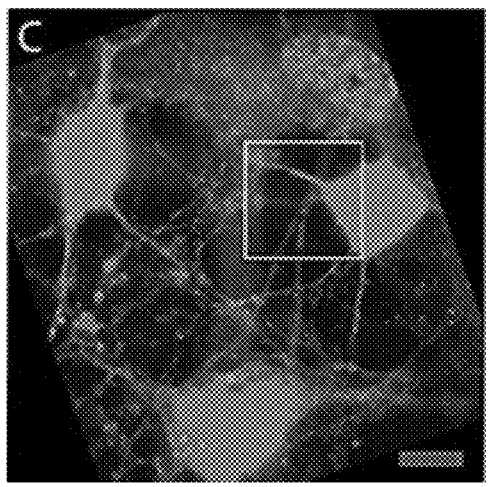
Figure 5D:
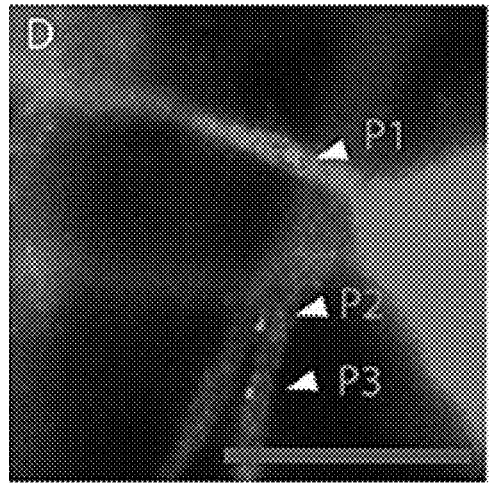
Figure 5E:
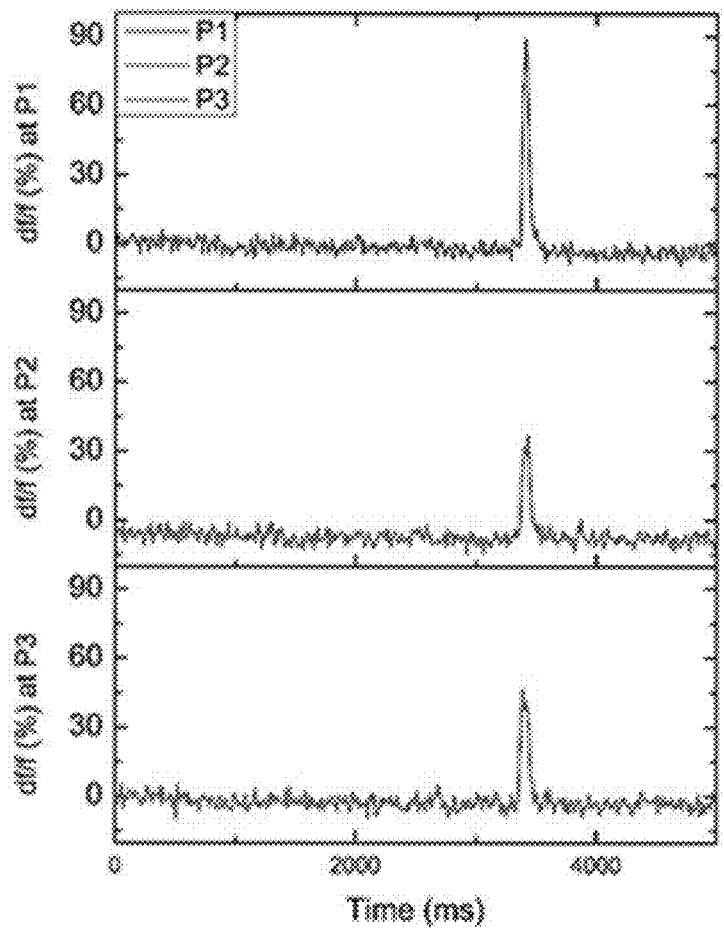

Having STARC-GCaMP6f in discretized puncta permitted imaging the activity over entire networks at subcellular resolution. To demonstrate this application, STARC-GCaMP6f was expressed in mice hippocampal neurons (FIG. 5A, B) and imaged the activity of all STARC-GCaMP6f puncta (FIG. 5E). Experimental methods included those described herein in addition to others described in Examples 1-3.

The stochastic distribution of STARC-GCaMP6f puncta could not delineate the network, so mCherry was co-expressed in the same neurons where STARC-GCaMP6f was expressed. FIG. 5A shows results obtained from in vitro culture of mice hippocampal neurons co-expressing STARC-GCaMP6f and mCherry. FIG. 5B is an expanded view of a representative region from the inset region shown in FIG. 5A (inset). Three STARC-GCaMP6f puncta of interest are denoted by white arrowheads (P1, P2, P3). The cells were imaged for 50 s and activity was recorded using standard procedures.

After live recording of activity, the neural culture was fixed and expansion microscopy was applied to enable tracing of individual neural projections at super-resolution by tracing mCherry of individual neurons. FIG. 5C-D demonstrates that expansion microscopy enhances resolution of closely located neural processes, enabling unambiguous attribution of STARC-GCaMP6f puncta. FIG. 5C shows post-expanded area of interest that corresponds to FIG. 5A. FIG. 5D shows post-expanded area of interest that corresponds to FIG. 5B. FIG. 5E shows activity plots of the STARC-GCaMP6f puncta of interest after attribution to cell 1 and cell 2. Results showed that each STARC-GCaMP6f punctum was attributed to its cell. This method of unambiguous attribution of individual STARC-GCaMP6f puncta and their associated activity to individual neurons enables sub-cellular physiological imaging of the entire network. The experimental results showed that STARE-GCaMP6f permits unambiguous attribution of neural activity within dense networks of neural processes in vitro.

Example 5

STARC-GCaMP6f Puncta Respond to Visual Stimulus In Vivo

Figure 6A:
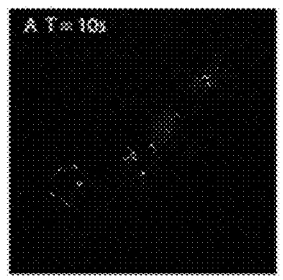
FIG. 6A-G shows photomicrographic images, graphs, and plots demonstrating that STARC-GCaMP6f puncta respond to visual stimulation in V1.
Figure 6B:
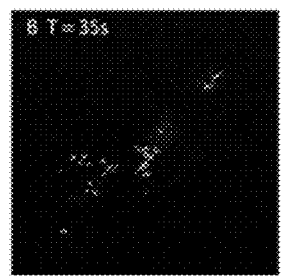
Figure 6C:
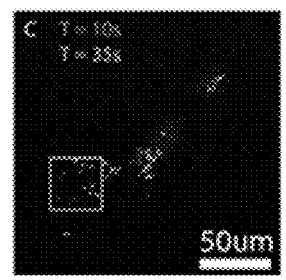
Figure 6D:
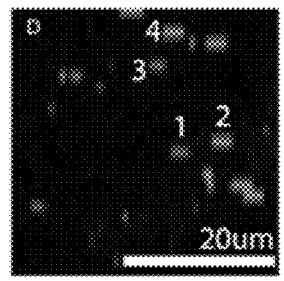
Figure 6E:
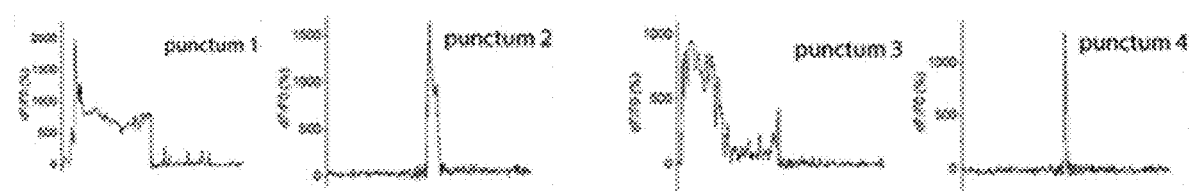
Figure 6F:
Figure 6G:
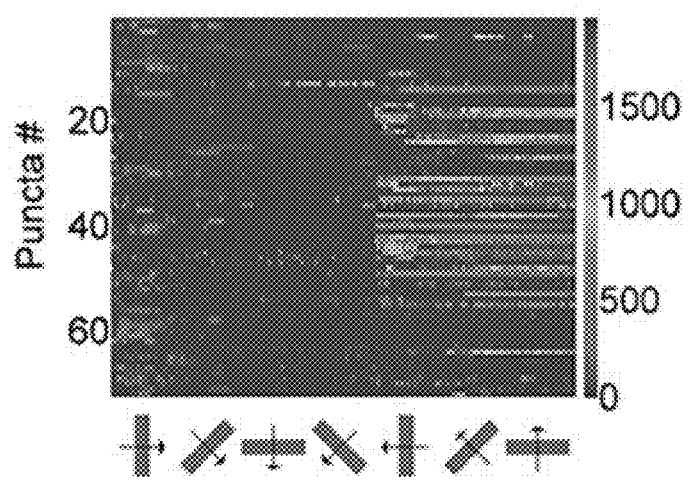

To assess the relevance of this new tool to in vivo studies STARC-GCaMP6f was expressed in the visual cortex (V1) of 5 week old mice by viral injection. The mouse was presented with moving grating, under 2p imaging. Experimental methods included those described herein in addition to others set forth in Examples 1-4. It has been previously established that the V1 responds to visual stimuli (Akerboom J, et al., 2012 J Neurosci. October 3; 32(40):13819-40). The V1 response to visual stimuli was examined using STARC-GCaMP6f expressed in the visual cortex. Following expression of the STARC compound in the mouse visual cortex, a cranial window was made, through which the STARC-GCaMP6f was imaged. Imaging was performed under conditions with and without application of visual stimulation. During the experiments, moving gratings were presented as previously described in Akerboom J, et al., 2012 J Neurosci. October 3; 32(40):13819-40) and Gong Y, et al., 2015 Science. 2015 Dec. 11; 350(6266):1361-6. Eight such experiments were performed and results showed that the STARC-GCaMP6f puncta could be readily observed (FIG. 6A-C). FIG. 6A shows the field of view at 10 s. FIG. 6B shows the field of view after 35 s. FIG. 6C shows an overlay of FIG. 6A and FIG. 6B. In all experiments the STARC-GCaMP6f puncta were responding to the moving gratings (FIG. 6D-F). FIG. 6D shows an expanded view of the insert in FIG. 6C and shows the response of single puncta during the experiment. The localization of puncta 1-4 is denoted in numbers in FIG. 6E and FIG. 6F provides an overlay of the responses of puncta 1-4 over time. The grating stimuli are given on the x axis. FIG. 6F provides a df/f0 analysis of the responses of all puncta in the field of view during the experiment. Results indicated that indicated that 51% (out of 1277 puncta) of the puncta in the field of views responded to stimuli, and that the df/f0 of the puncta was ranging between 50%-1500%. In the studies, it was observed that some of the puncta showed preference towards a specific stimulation vs. the others, an example of which is shown in FIG. 6F.

Example 6

STARC Translocation Studies

Figures 7A, 7B, 7C:
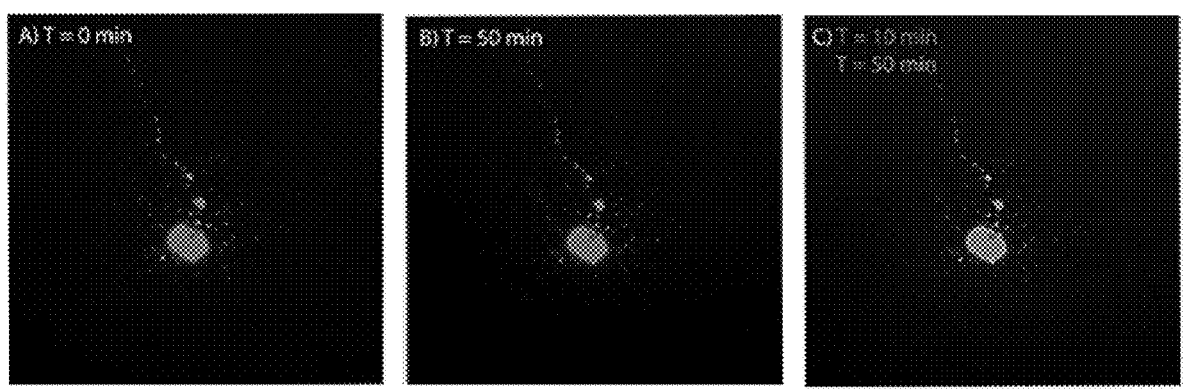
FIG. 7A-C provides photomicrographic images demonstrating that STARC-GCaMP6f puncta do not translocate.

Studies were performed to assess STARC molecules to determine whether or not they translocated once present in cells. Experimental methods included those described herein in addition to others set forth in Examples 1-5. FIG. 7A-C provides photomicrographic images of results from the studies, which demonstrated that STARC-GCaMP6f puncta do not translocate. FIG. 7A shows imaged neuron expressing STARC-GCaMP6 and FIG. 7B shows the same neuron, imaged again 50 minutes after the image shown in FIG. 7A was obtained. FIG. 7C is an overlay of the FIGS. 7A and 7B images (T=0, 50 min) and indicate that there was negligible movement of the STARC-GCaMP6 puncta during the time period between imaging.

EQUIVALENTS

It is to be understood that the methods and compositions that have been described above are merely illustrative applications of the principles of the invention. Numerous modifications may be made by those skilled in the art without departing from the scope of the invention.

Although the invention has been described in detail for the purpose of illustration, it is understood that such detail is solely for that purpose and variations can be made by those skilled in the art without departing from the spirit and scope of the invention which is defined by the following claims.

The contents of all literature references, publications, patents, and published patent applications cited throughout this application are incorporated herein by reference in their entirety.

What is claimed:

1. A composition comprising an activity reporter polypeptide wherein the activity reporter polypeptide is a fusion protein comprising:
   (a) two or more different binding domains;
   (b) an indicator polypeptide; and
   (c) a linker polypeptide, wherein the linker is between the indicator polypeptide and the binding domains,
   wherein at least two of the different binding domains bind different specific binding partner polypeptide molecules and when these at least two binding domains of two or more activity reporter polypeptides bind to their binding partner polypeptide molecules the activity reporter polypeptides are attached to each other through the binding partner polypeptide molecules.

2. The composition of claim 1, wherein the two or more different binding domains comprise myosin binding domains, each capable of binding its specific myosin binding partner polypeptide molecule.

3. The composition of claim 1, wherein at least one of the binding domains is a myosin binding domain.

4. The composition of claim 1, wherein the indicator polypeptide comprises a fluorescent polypeptide.

5. The composition of claim 1, wherein the indicator polypeptide is a voltage indicator polypeptide, a calcium indicator polypeptide, a potassium indicator polypeptide, a pH indicator polypeptide, or a magnesium indicator polypeptide.

6. The composition of claim 1, wherein the indicator polypeptide is an opsin or a GCaMP6f polypeptide.

7. The composition of claim 1, wherein when expressed in a cell, the indicator polypeptide is soluble in the cell.

8. The composition of claim 1, wherein when expressed in a cell, the indicator polypeptide is a membranal polypeptide.

9. A fusion protein comprising the activity reporter polypeptide of claim 1.

10. A polynucleotide encoding the composition of claim 1.

11. An expression vector comprising the polynucleotide of claim 10.

12. A cell comprising the composition of claim 1.

13. A method of imaging in a cell, the method comprising: expressing in a first cell, an activity reporter polypeptide wherein the activity reporter polypeptide is a fusion protein comprising:
   (a) two or more different binding domains;
   (b) an indicator polypeptide; and
   (c) a linker polypeptide, wherein the linker is between the indicator polypeptide and the binding domains,
   wherein at least two of the different binding domains bind different specific binding partner polypeptide molecules and when these at least two binding domains of two or more activity reporter polypeptides bind to their binding partner polypeptide molecules the activity reporter polypeptides are attached to each other through the binding partner polypeptide molecules;
   and imaging the first cell with a microscope.

14. The method of claim 13, further comprising expressing in a second cell a second, different, activity reporter polypeptide wherein the second activity reporter polypeptide is a fusion protein comprising:
   (d) two or more different binding domains;
   (e) an indicator polypeptide; and
   (f) a linker polypeptide, wherein the linker is between the indicator polypeptide and the binding domains,
   wherein at least two of the different binding domains bind different specific binding partner polypeptide molecules and when these at least two binding domains of two or more of the second activity reporter polypeptides bind to their binding partners polypeptide molecules the second activity reporter polypeptides are attached to each other through the binding partner polypeptide molecules;
   and imaging the first cell and the second cell with a microscope.

15. The method of claim 13, wherein the indicator polypeptide is a voltage indicator polypeptide, a calcium indicator polypeptide, a potassium indicator polypeptide, a pH indicator polypeptide, or a magnesium indicator polypeptide.

16. A method of assessing an activity indicated by an indicator polypeptide in a cell, the method comprising:
   (a) expressing in a cell, more than one of an activity reporter polypeptide wherein the activity reporter polypeptide is a fusion protein comprising:
      (i) two or more different binding domains;
      (ii) an indicator polypeptide; and
      (iii) a linker polypeptide, wherein the linker is between the indicator polypeptide and the binding domains,
      wherein at least two of the different binding domains bind different specific binding partner polypeptide molecules and when these at least two binding domains of two or more activity reporter polypeptides bind to their binding partner polypeptide molecules the activity reporter polypeptides are attached to each other through the binding partner polypeptide molecules;
   (b) imaging the indicator polypeptide in the cell; and
   (c) assessing the activity indicated by the indicator polypeptide in the cell, based at least in part on the imaging of the indicator polypeptide in the cell.

17. The method of claim 16, further comprising
   (d) contacting the cell with a candidate agent;
   (e) imaging the activity reporter polypeptides in the cell;
   (f) assessing the activity in the cell-based at least in part on the imaging of (e); and
   (g) comparing the assessment of (f) with a control activity in the cell not contacted with the candidate agent, wherein a difference between the activity in the contacted cell as assessed in (f) and the control activity determines an effect of the candidate agent on the activity in the cell.

18. The method of claim 17, wherein the indicator polypeptide is a voltage indicator polypeptide, a calcium indicator polypeptide, a potassium indicator polypeptide, a pH indicator polypeptide, or a magnesium polypeptide.

19. The method of claim 17, wherein the indicator polypeptide comprises a fluorescent polypeptide.

* * * * *